United States Patent
Mizuno et al.

(10) Patent No.: US 7,223,769 B2
(45) Date of Patent: May 29, 2007

(54) PYRIMIDINE COMPOUNDS AND THEIR USE AS PESTICIDES

(75) Inventors: Hajime Mizuno, Toyonaka (JP); Noriyasu Sakamoto, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 465 days.

(21) Appl. No.: 10/506,209

(22) PCT Filed: Mar. 4, 2003

(86) PCT No.: PCT/JP03/02464

§ 371 (c)(1), (2), (4) Date: Sep. 1, 2004

(87) PCT Pub. No.: WO03/076415

PCT Pub. Date: Sep. 18, 2003

(65) Prior Publication Data

US 2005/0171130 A1    Aug. 4, 2005

(30) Foreign Application Priority Data

Mar. 12, 2002    (JP)    ............................ 2002-066612

(51) Int. Cl.
C07D 239/52    (2006.01)
A01N 43/54    (2006.01)
(52) U.S. Cl. ...................................... 514/269; 544/319
(58) Field of Classification Search ................ 544/319; 514/269
See application file for complete search history.

(56) References Cited

U.S. PATENT DOCUMENTS 5,859,020 A    1/1999    Preuss et al.

FOREIGN PATENT DOCUMENTS

| EP | 0 534 341 A | 3/1993 |
|---|---|---|
| EP | 0 639 571 A | 2/1995 |
| JP | 60-13769 A | 1/1985 |
| JP | 04-95077 A | 3/1992 |
| WO | WO 01/07027 A2 | 2/2001 |
| WO | WO 01/07027 A3 | 2/2001 |
| WO | WO 02/24663 A | 3/2002 |

*Primary Examiner*—Deepak Rao
(74) *Attorney, Agent, or Firm*—Sughrue Mion, PLLC

(57) ABSTRACT

The present invention relates to a pyrimidine compound of formula (1):

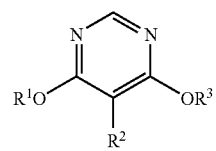

(1)

wherein $R^1$ is $C_3$–$C_7$ alkynyl; $R^2$ is hydrogen, halogen, or $C_1$–$C_3$ alkyl; and $R^3$ is $C_1$–$C_8$ alkyl that may be substituted with halogen or $C_1$–$C_3$ alkoxy, or $C_3$–$C_6$ cycloalkyl (that may be substituted with halogen or $C_1$–$C_3$ alkyl) $C_1$–$C_3$ alkyl; a pesticidal composition comprising the pyrimidine compound as an active ingredient; and a method for controlling pests comprising applying the pyrimidine compound to pests or habitats of pests.

6 Claims, No Drawings

PYRIMIDINE COMPOUNDS AND THEIR USE AS PESTICIDES

This application is a national stage application of PCT/JP03/02464 filed Mar. 4, 2003.

TECHNICAL FIELD

The present invention relates to pyrimidine compounds and their use.

BACKGROUND ART

Various compounds have been developed so far to control pests and they have been put into practice. Some of these compounds cannot always exhibit satisfactory activity.

It is an objective of the present invention to provide novel compounds having pesticidal activity.

DISCLOSURE OF INVENTION

The present inventors have intensively studied to find compounds having excellent pesticidal activity, and as a result, they have found that the compounds of formula (1) as depicted below have excellent pesticidal activity, thereby completing the present invention.

Thus the present invention provides a pyrimidine compound of formula (1):

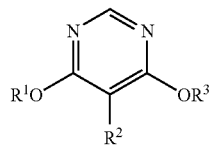

(1)

(hereinafter referred to as the present compound(s))
wherein $R^1$ is $C_3$–$C_7$ alkynyl; $R^2$ is hydrogen, halogen, or $C_1$–$C_3$ alkyl; and $R^3$ is $C_1$–$C_8$ alkyl that may be substituted with halogen or $C_1$–$C_3$ alkoxy, or $C_3$–$C_6$ cycloalkyl— (that may be substituted with halogen or $C_1$–$C_3$ alkyl) $C_1$–$C_3$ alkyl; a pesticidal composition comprising the present compound as an active ingredient; and a method for controlling pests comprising applying the present compound to pests or habitats of pests.

MODE FOR CARRYING OUT THE INVENTION

In the definition of substituents as used herein, each group has the following meaning:

The $C_3$–$C_7$ alkynyl represented by $R^1$ may include, for example, $C_3$–$C_7$ alkynyl in which the bond between the carbon atoms at positions 2 and 3 is a triple bond. Specific examples are 2-propynyl, 2-butynyl, 1-methyl-2-butynyl, 2-pentynyl, 1-methyl-2-pentynyl, 4,4-dimethyl-2-pentynyl, 1-methyl-2-propynyl, and 1,1-dimethyl-2-propynyl.

The $C_1$–$C_3$ alkyl represented by $R^2$ may include, for example, methyl and ethyl. The halogen may include, for example, fluorine and chlorine.

In the $C_1$–$C_8$ alkyl that may be substituted with halogen or $C_1$–$C_3$ alkoxy, represented by $R^3$, the halogen may include, for example, fluorine, chlorine, and bromine, and the $C_1$–$C_3$ alkoxy may include, for example, methoxy, ethoxy, propoxy, and isopropoxy.

The $C_1$–$C_8$ alkyl that may be substituted with halogen or $C_1$–$C_3$ alkoxy, represented by $R^3$, may include, for example, $C_3$–$C_8$ branched alkyl that may be substituted with halogen or $C_1$–$C_3$ alkoxy. Specific examples are as follows:
isopropyl, isobutyl, sec-butyl, 1,2-dimethylpropyl, isopentyl, neopentyl, 1-methylbutyl, 2-methylbutyl, 1-ethylpropyl, 1,2,2-trimethylpropyl, 1,2-dimethylbutyl, 1-ethyl-2-methylpropyl, 2,3-dimethylbutyl, 3,3-dimethylbutyl, 1-methylpentyl, 2-methylpentyl, 3-methylpentyl, isohexyl, 2-ethylbutyl, 1,3-dimethylbutyl, 2,2-dimethylbutyl, 1-ethyl-2,2-dimethylpropyl, 1,3,3-trimethylbutyl 2,3,3-trimethylbutyl, 1-isopropyl-2-methylpropyl, 1-ethyl-3,3-dimethylbutyl, 1,2,3,3-tetramethylbutyl, 1-methyl-2,2-dimethoxyethyl, 1-methyl-2,2,2-trichloroethyl, 1-methyl-2,2,2-trifluoroethyl, 1-methyl-2,2-dichloroethyl, 1-methyl-2,2-difluoroethyl, 2-methyl-2-methyloxypropyl, 1-methyl-2-chloroethyl, 1-methyl-2-fluoroethyl, 1-methyl-2-isopropyloxyethyl, 1-methyl-2-chloropropyl, 1-methyl-2-fluoropropyl, 1-methyl-2,2-dichloropropyl, 1-methyl-2,2-difluoropropyl, 2-chloro-2-methylpropyl, 2-fluoro-2-methylpropyl, 2-bromo-2-methylpropyl, 3-fluoro-2-methylpropyl, 3-chloro-2-methylpropyl, 2,3-dichloro-2-methylpropyl, 1,2-dimethyl-2-methyloxypropyl, 3-bromo-2,2-dimethylpropyl, 3-chloro-2,2-dimethylpropyl, 2,2-dichloro-2-fluoro-1-methylethyl, 3-fluoro-2,2-dimethylpropyl, 2,3-dichloro-1,2-dimethylpropyl, 1,2-dimethyl-2-fluoropropyl, 1,2-dimethyl-2-chloropropyl, 1,2-dimethyl-2-bromopropyl, 3-fluoro-1,2-dimethylpropyl, 3-chloro-1,2-dimethylpropyl, 3,3-difluoro-1,2-dimethylpropyl, 3,3,3-trifluoro-2-trifluoromethyl-2-methylpropyl, 2,2-dichloro-1-isopropylethyl, 2,2,2-trifluoro-1-isopropylethyl, 2,2-difluoro-1-isopropylethyl, 2,2,2-trichloro-1-(t-butyl)ethyl, 2,2-dichloro-1-(t-butyl)ethyl, 3-fluoro-1,3-dimethylbutyl, 3-chloro-1,3-dimethylbutyl, 3-bromo-1,3-dimethylbutyl, 3-fluoro-2,3-dimethylbutyl, 3-chloro-2,3-dimethylbutyl, 3-bromo-2,3-dimethylbutyl, 3-fluoro-1,2,2-trimethylpropyl, 3-chloro-1,2,2-trimethylpropyl, 3-bromo-1,2,2-trimethylpropyl, 2-fluoro-1-ethyl-2-methylpropyl, 2-bromo-1-ethyl-2-methylpropyl, 2-chloro-1-ethyl-2-methylpropyl, 1-trichloromethyl-2-methylpropyl, 2,2,2-trichloro-1-chloromethylethyl, 2,2-dichloro-1-dichloromethylethyl, 1-trichloromethylpropyl, 2,2-dichloro-1-ethylpropyl, 2,2-dichloro-2-fluoroethyl, 2,2-dichloro-1-trifluoromethylethyl, 3,3,3-trichloroethyl, and 3,3,3-trifluoropropyl.

In the $C_3$–$C_6$ cycloalkyl—(that may be substituted with halogen or $C_1$–$C_3$ alkyl) $C_1$–$C_3$ alkyl, represented by $R^3$, the halogen may include, for example, fluorine, chlorine, and bromine, and the $C_1$–$C_3$ alkyl may include, for example, methyl and ethyl.

The $C_3$–$C_6$ cycloalkyl—(that may be substituted with halogen or $C_1$–$C_3$ alkyl) $C_1$–$C_3$ alkyl represented by $R^3$ may include, for example, cyclopropylmethyl, 1-(cyclopropyl)ethyl, 2-(cyclopropyl)ethyl, 1-(1-methylcyclopropyl)ethyl, 2-(1-methylcyclopropyl)ethyl, 1-(2-ethylcyclopropyl)ethyl, 2-(2-ethylcyclopropyl)ethyl, 1-(2-fluorocyclopropyl)ethyl, 2-(2-fluorocyclopropyl)ethyl, 1-(2-chlorocyclopropyl)ethyl, 2-(2-chlorocyclopropyl)ethyl, 1-(1,2-dimethylcyclopropyl)ethyl, 2-(1,2-dimethylcyclopropyl)ethyl, 1-(2,2-dimethylcyclopropyl)ethyl, 2-(2,2-dimethylcyclopropyl)ethyl, 1-(2,2-dichloro-1-methylcyclopropyl)ethyl, 2-(2,2-dichloro-1-methylcyclopropyl)ethyl, 1-(2,2-dichloro-3,3-dimethylcyclopropyl)ethyl, 2-(2,2-dichloro-3,3-dimethylcyclopropyl)ethyl, 1-(cyclobutyl)ethyl, 2-(cyclobutyl)ethyl, 1-(1-methylcyclobutyl)ethyl, 2-(1-methylcyclobutyl)ethyl, 1-(2-methylcyclobutyl)ethyl, 2-(2-methylcyclobutyl)ethyl, 1-(1-chlorocyclobutyl)ethyl, 2-(1-chlorocyclobutyl)ethyl, 1-(2-chlorocyclobutyl)ethyl, 2-(2- chlorocyclobutyl)ethyl, 1-(2,2-difluorocyclobutyl)ethyl, 2-(2,2-difluorocyclobutyl)ethyl, 1-(cyloropentyl)ethyl, 2-(cyloropentyl)ethyl, 1-(1-methylcyloropentyl)ethyl, 2-(1-methylcyloropentyl)ethyl, 1-(2-methylcyloropentyl)ethyl, 2-(2-methylcyloropentyl)ethyl, 1-(2-ethylcyloropentyl) ethyl, 2-(2-ethylcyloropentyl)ethyl, 1-(2-fluorocyloropentyl)ethyl, 2-(2-fluorocyloropentyl)ethyl, 1-(2-chlorocyloropentyl)ethyl, 2-(2-chlorocyclopentyl)ethyl, 1-(2-bromocyclopentyl)ethyl, 2-(2-bromocyclopentyl)ethyl, 1-(1,2-dimethylcyclopentyl)ethyl, 2-(1,2-dimethylcyclopentyl)ethyl, 1-(3-methylcyclopentyl)ethyl, 2-(3-methylcyclopentyl)ethyl, 1-(3-fluorocyclopentyl)ethyl, 2-(3-fluorocyclopentyl)ethyl, 1-(3-chlorocyclopentyl)ethyl, 2-(3-chlorocyclopentyl)ethyl, 1-(cylcohexyl)ethyl, and 2-(cylcohexyl)ethyl.

The embodiments of the present compounds may include, for example, the following compounds:

the compounds of formula (1) wherein $R^1$ is $C_3$–$C_7$ alkynyl in which the bond between the carbon atoms at positions 2 and 3 is a triple bond;

the compounds of formula (1) wherein $R^1$ is 2-propynyl, 2-butynyl, 1-methyl-2-butynyl, or 2-pentynyl;

the compounds of formula (1) wherein $R^2$ is hydrogen;

the compounds of formula (1) wherein $R^3$ is $C_2$–$C_8$ alkyl that may be substituted with halogen;

the compounds of formula (1) wherein $R^3$ is $C_3$–$C_8$ branched alkyl that may be substituted with halogen or $C_1$–$C_3$ alkoxy;the compounds of formula (1) wherein $R^3$ is $C_3$–$C_6$ cycloalkyl—(that may be substituted with halogen or $C_1$–$C_3$ alkyl) $C_1$–$C_3$ alkyl;

the compounds of formula (1) wherein $R^1$ is $C_3$–$C_7$ alkynyl in which the bond between the carbon atoms at positions 2 and 3 is a triple bond; $R^2$ is hydrogen; and $R^3$ is $C_3$–$C_8$ alkyl that may be substituted with halogen;

the compounds of formula (1) wherein $R^1$ is $C_3$–$C_7$ alkynyl in which the bond between the carbon atoms at positions 2 and 3 is a triple bond; $R^2$ is hydrogen; and $R^3$ is $C_3$–$C_8$ branched alkyl that may be substituted with halogen;

the compounds of formula (1) wherein $R^1$ is $C_3$–$C_7$ alkynyl in which the bond between carbon atoms at positions 2 and 3 is a triple bond; $R^2$ is hydrogen; $R^3$ is $C_3$–$C_6$ cycloalkyl—(that may be substituted with halogen or $C_1$–$C_3$ alkyl) $C_1$–$C_3$ alkyl;

the compounds of formula (1) wherein $R^1$ is $C_3$–$C_7$ alkynyl in which the bond between carbon atoms at positions 2 and 3 is a triple bond; $R^2$ is hydrogen; $R^3$ is methyl substituted with $C_3$–$C_6$ cycloalkyl that may be substituted with halogen or $C_1$–$C_3$ alkyl;

the compounds of formula (1) wherein $R^1$ is $C_3$–$C_7$ alkynyl in which the bond between carbon atoms at positions 2 and 3 is a triple bond; $R^2$ is hydrogen; $R^3$ is ethyl substituted on the carbon atom at position 1 with $C_3$–$C_6$ cycloalkyl that may be substituted with halogen or $C_1$–$C_3$ alkyl;

the compounds of formula (1) wherein $R^1$ is $C_3$–$C_7$ alkynyl in which the bond between carbon atoms at positions 2 and 3 is a triple bond; $R^2$ is hydrogen; $R^3$ is ethyl substituted on the carbon atom at position 2 with $C_3$–$C_6$ cycloalkyl that may be substituted with halogen or $C_1$–$C_3$ alkyl;

the compounds of formula (1) wherein $R^1$ is $C_3$–$C_7$ alkynyl in which the bond between carbon atoms at positions 2 and 3 is a triple bond; $R^2$ is hydrogen; $R^3$ is propyl substituted on the carbon atom at position 1 with $C_3$–$C_6$ cycloalkyl that may be substituted with halogen or $C_1$–$C_3$ alkyl; and the compounds of formula (1) wherein $R^1$ is $C_3$–$C_7$ alkynyl in which the bond between carbon atoms at positions 2 and 3 is a triple bond; $R^2$ is hydrogen; $R^3$ is propyl substituted on the carbon atom at position 2 with $C_3$–$C_6$ cycloalkyl that may be substituted with halogen or $C_1$–$C_3$ alkyl.

The following will describe a production process for the present compound.

(Production Process)

The present compound of formula (1) can be produced from a 4,6-dichloropyrimidine compound of formula (2) via the following steps:

wherein $R^1$, $R^2$, and $R^3$ are as defined above.

Step (1-1)

The compound of formula (3) can be produced by reacting a 4,6-dichloropyrimidine compound of formula (2) with an alcohol compound of formula (4):

$$R^3OH \quad\quad\quad (4)$$

wherein $R^3$ is as defined above.

The reaction is usually carried out in a solvent in the presence of a base.

The solvent that can be used in the reaction may include, for example, ethers such as tetrahydrofuran, diethyl ether, and methyl t-butyl ether; acid amides such as N,N-dimethylformamide; sulfoxides such as dimethylsulfoxide; and mixtures thereof.

The base that can be used in the reaction may include, for example, inorganic bases such as sodium hydride; alkali metal carbonates such as potassium carbonate and sodium carbonate; and organic lithium compounds such as n-butyl lithium. The amount of the base that can be used in the reaction is usually in the ratio of 1 to 2.5 moles per mole of the 4,6-dichloropyrimidine compound of formula (2).

The amount of the alcohol compound of the formula (4) that can be used in the reaction is usually in the ratio of 1 to 1.5 moles per mole of the 4,6-dichloropyrimidine compound of formula (2).

The reaction temperature is usually in the range of 0° C. to 80° C., and the reaction time is usually in the range of 0.1 to 12 hours.

After completion of the reaction, the reaction mixture is subjected to ordinary post-treatment procedures such as extraction with an organic solvent, drying the organic layer, and subsequent concentration, to isolate the compound of formula (3). The compound of formula (3) thus isolated can be purified by a technique such as chromatography.

Step (1-2)

The present compound of formula (1) can be produced by reacting the compound of formula (3) with an alcohol compound of formula (5):

$$R^1OH \quad (5)$$

wherein $R^1$ is as defined above.

The reaction is usually in a solvent in the presence of a base.

The solvent that can be used in the reaction may include, for example, ethers such as tetrahydrofuran, diethyl ether, and methyl t-butyl ether; acid amides such as N,N-dimethylformamide; sulfoxides such as dimethylsulfoxide; and mixtures thereof.

The base that can be used in the reaction may include, for example, inorganic bases such as sodium hydride. The amount of the base that can be used in the reaction is usually in the ratio of 1 to 2.5 moles per mole of the compound of formula (3).

The amount of the alcohol compound of the formula (5) that can be used in the reaction is usually in the ratio of 1 to 1.5 moles per mole of the compound of formula (3).

The reaction temperature is usually in the range of 0° C. to 80° C., and the reaction time is usually in the range of 0.1 to 12 hours.

After completion of the reaction, the reaction mixture is subjected to ordinary post-treatment procedures such as extraction with an organic solvent, drying the organic layer, and subsequent concentration, to isolate the present compound of formula (1). The present compound of formula (1) thus isolated can be purified by a technique such as chromatography.

Specific examples of the present compound are listed below:

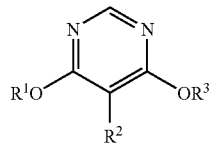

(1)

The compounds of formula (1) wherein $R^1$ is 2-propynyl; $R^2$ is hydrogen; and $R^3$ is any of the following substituents:

isobutyl, 1,2-dimethylpropyl, isopentyl, neopentyl, 1,2,2-trimethylpropyl, 1-ethyl-2-methylpropyl, 3,3-dimethylbutyl, 1,3-dimethylbutyl, 1-ethyl-2,2-dimethylpropyl, 1-methyl-2,2,2-trichloroethyl, 1-methyl-2,2-dichloroethyl, 1-methyl-2,2-difluoroethyl, 1-methyl-2-chloropropyl, 1-methyl-2,2-dichloropropyl, 1-methyl-2,2-difluoropropyl, 2-chloro-2-methylpropyl, 2-fluoro-2-methylpropyl, 2-bromo-2-methylpropyl, 3-fluoro-2-methylpropyl, 3-chloro-2-methylpropyl, 2,3-dichloro-2-methylpropyl, 3-bromo-2,2-dimethylpropyl, 3-chloro-2,2-dimethylpropyl, 3-fluoro-2,2-dimethylpropyl, 2,3-dichloro-1,2-dimethylpropyl, 1,2-dimethyl-2-fluoroethyl, 1,2-dimethyl-2-chloroethyl, 1,2-dimethyl-2-bromoethyl, 3-fluoro-1,2-dimethylpropyl, 3-chloro-1,2-dimethylpropyl, 3,3-difluoro-1,2-dimethylpropyl, 1-dichloromethyl-2-methylpropyl, 1-dichloromethyl-2-methylpropyl, 2,2-dimethyl-1-trichloromethyl, 2,2-dimethyl-1-dichloromethylpropyl, 3-fluoro-1,2,2-trimethylpropyl, 3-chloro-1,2,2-trimethylpropyl, 2-fluoro-1-ethyl-2-methylpropyl, 2-bromo-1-ethyl-2-methylpropyl, 2-chloro-1-ethyl-2-methylpropyl, 2-methyl-2-methyloxypropyl, 1,2-dimethyl-2-methyloxypropyl, 2,2-dichloro-2-fluoro-1-methylethyl, or 2-methyl-1-trichloromethylpropyl.

The compounds of formula (1) wherein $R^1$ is 2-butynyl; $R^2$ is hydrogen; and $R^3$ is any of the following substituents:

isopropyl, isobutyl, sec-butyl, 1,2-dimethylpropyl, isopentyl, neopentyl, isohexyl, 1,2,2-trimethylpropyl, 1,2-dimethylbutyl, 1-ethyl-2-methylpropyl, 2,3-dimethylbutyl, 2,2-dimethylbutyl, 3,3-dimethylbutyl, 1,3-dimethylbutyl, 1-ethyl-2,2-dimethylpropyl, 2,3,3-trimethylbutyl, 1,3,3-trimethylbutyl, 1-ethyl-3,3-dimethylbutyl, 1,2,3,3-tetramethylbutyl, 1-methyl-2,2-dimethoxyethyl, 1-methyl-2,2,2-trichloroethyl, 1-methyl-2,2,2-trifluoromethyl, 1-methyl-2,2-dichloroethyl, 1-methyl-2,2-difluoroethyl, 1-methyl-2-chloroethyl, 1-methyl-2-fluoroethyl, 1-methyl-2-isopropoxyethyl, 1-methyl-2-chloropropyl, 1-methyl-2-fluoropropyl, 1-methyl-2,2-dichloropropyl, 1-methyl-2,2-difluoropropyl, 2-chloro-2-methylpropyl, 2-fluoro-2-methylpropyl, 2-bromo-2-methylpropyl, 3-fluoro-2-methylpropyl, 3-chloro-2-methylpropyl, 2,3-dichloro-2-methylpropyl, 3-bromo-2,2-dimethylpropyl, 3-chloro-2,2-dimethylpropyl, 3-fluoro-2,2-dimethylpropyl, 2,3-dichloro-1,2-dimethylpropyl, 1,2-dimethyl-2-fluoroethyl, 1,2-dimethyl-2-chloroethyl, 1,2-dimethyl-2-bromoethyl, 3-fluoro-1,2-dimethylpropyl, 3-chloro-1,2-dimethylpropyl, 3,3-difluoro-1,2-dimethylpropyl, 3,3,3-trifluoro-2-trifluoromethyl-2-methylpropyl, 1-dichloromethyl-2-methylpropyl, 1-trifluoromethyl-2-methylpropyl, 1-dichloromethyl-2-methylpropyl, 2,2-dimethyl-1-trichloromethylpropyl, 2,2-dimethyl-1-dichloromethylpropyl, 3-fluoro-1,3-dimethylbutyl, 3-chloro-1,3-dimethylbutyl, 3-bromo-1,3-dimethylbutyl, 3-fluoro-2,3-dimethylbutyl, 3-chloro-2,3-dimethylbutyl, 3-bromo-2,3-dimethylbutyl, 3-fluoro-1,2,2-trimethylpropyl, 3-chloro-1,2,2-trimethylpropyl, 3-bromo-1,2,2-trimethylpropyl, 2-fluoro-1-ethyl-2-methylpropyl, 2-bromo-1-ethyl-2-methylpropyl, 2-chloro-1-ethyl-2-methylpropyl, 2-methyl-2-methoxypropyl, 1,2-dimethyl-2-methoxypropyl, 2,2-dichloro-2-fluoro-1-methylethyl, or 2-methyl-1-trichloromethylpropyl.

The compounds of formula (1) wherein $R^1$ is 2-butynyl; $R^2$ is methyl; and $R^3$ is any of the following substituents:

isobutyl, 1,2-dimethylpropyl, isopentyl, neopentyl, 1,2,2-trimethylpropyl, 1-ethyl-2-methylpropyl, 3,3-dimethylbutyl, 1,3-dimethylbutyl, 1-ethyl-2,2-dimethylpropyl, 1-methyl-2,2,2-trichloroethyl, 1-methyl-2,2-dichloroethyl, 1-methyl-2,2-difluoroethyl, 1-methyl-2-chloropropyl, 1-methyl-2,2-dichloropropyl, 1-methyl-2,2-difluoropropyl, 2-chloro-2-methylpropyl, 2-fluoro-2-methylpropyl, 2-bromo-2-methylpropyl, 3-fluoro-2-methylpropyl, 3-chloro-2-methylpropyl, 2,3-dichloro-2-methylpropyl, 3-bromo-2,2-dimethylpropyl, 3-chloro-2,2-dimethylpropyl, 3-fluoro-2,2-dimethylpropyl, 2,3-dichloro-1,2-dimethylpropyl, 1,2-dimethyl-2-fluoroethyl, 1,2-dimethyl-2-chloroethyl, 1,2-dimethyl-2-bromoethyl, 3-fluoro-1,2-dimethylpropyl, 3-chloro-1,2-dimethylpropyl, 3,3-difluoro-1,2-dimethylpropyl, 1-dichloromethyl-2-methylpropyl, 1-dichloromethyl-2-methylpropyl, 2,2-dimethyl-1-trichloromethyl, 2,2-dimethyl-1-dichloromethylpropyl, 3-fluoro-1,2,2-trimethylpropyl, 3-chloro-1,2,2-trimethylpropyl, 2-fluoro-1-ethyl-2-methylpropyl, 2-bromo-1-ethyl-2-methylpropyl, 2-chloro-1-ethyl-2-methylpropyl, 2-methyl-2-methyloxypropyl, 1,2-dimethyl-2-methyloxypropyl, 2,2-dichloro-2-fluoro-1-methylethyl, or 2-methyl-1-trichloromethylpropyl.

The compounds of formula (1) wherein $R^1$ is 2-butynyl; $R^2$ is chlorine; and $R^3$ is any of the following substituents:

isobutyl, 1,2-dimethylpropyl, isopentyl, neopentyl, 1,2,2-trimethylpropyl, 1-ethyl-2-methylpropyl, 3,3-dimethylbutyl, 1,3-dimethylbutyl, 1-ethyl-2,2-dimethylpropyl, 1-methyl-2,2,2-trichloroethyl, 1-methyl-2,2-dichloroethyl, 1-methyl-2,2-difluoroethyl, 1-methyl-2-chloropropyl, 1-methyl-2,2-dichloropropyl, 1-methyl-2,2-difluoropropyl, 2-chloro-2-methylpropyl, 2-fluoro-2-methylpropyl, 2-bromo-2-methylpropyl, 3-fluoro-2-methylpropyl, 3-chloro-2-methylpropyl, 2,3-dichloro-2-methylpropyl, 3-bromo-2,2-dimethylpropyl, 3-chloro-2,2-dimethylpropyl, 3-fluoro-2,2-dimethylpropyl, 2,3-dichloro-1,2-dimethylpropyl, 1,2-dimethyl-2-fluoroethyl, 1,2-dimethyl-2-chloroethyl, 1,2-dimethyl-2-bromoethyl, 3-fluoro-1,2-dimethylpropyl, 3-chloro-1,2-dimethylpropyl, 3,3-difluoro-1,2-dimethylpropyl, 1-dichloromethyl-2-methylpropyl, 1-dichloromethyl-2-methylpropyl, 2,2-dimethyl-1-trichloromethyl, 2,2-dimethyl-1-dichloromethylpropyl, 3-fluoro-1,2,2-trimethylpropyl, 3-chloro-1,2,2-trimethylpropyl, 2-fluoro-1-ethyl-2-methylpropyl, 2-bromo-1-ethyl-2-methylpropyl, 2-chloro-1-ethyl-2-methylpropyl, 2-methyl-2-methyloxypropyl, 1,2-dimethyl-2-methyloxypropyl, 2,2-dichloro-2-fluoro-1-methylethyl, or 2-methyl-1-trichloromethylpropyl.

The compounds of formula (1) wherein $R^1$ is 2-pentynyl; $R^2$ is hydrogen; and $R^3$ is any of the following substituents:
isopropyl, isobutyl, sec-butyl, 1,2-dimethylpropyl, isopentyl, neopentyl, isohexyl, 1,2,2-trimethylpropyl, 1,2-dimethylbutyl, 1-ethyl-2-methylpropyl, 2,3-dimethylbutyl, 2,2-dimethylbutyl, 3,3-dimethylbutyl, 1,3-dimethylbutyl, 1-ethyl-2,2-dimethylpropyl, 2,3,3-trimethylbutyl, 1,3,3-trimethylbutyl, 1-ethyl-3,3-dimethylbutyl, 1,2,3,3-tetramethylbutyl, 1-methyl-2,2-dimethoxyethyl, 1-methyl-2,2,2-trichloroethyl, 1-methyl-2,2,2-trifluoromethyl, 1-methyl-2,2-dichloroethyl, 1-methyl-2,2-difluoroethyl, 1-methyl-2-chloroethyl, 1-methyl-2-fluoroethyl, 1-methyl-2-isopropoxyethyl, 1-methyl-2-chloropropyl, 1-methyl-2-fluoropropyl, 1-methyl-2,2-dichloropropyl, 1-methyl-2,2-difluoropropyl, 2-chloro-2-methylpropyl, 2-fluoro-2-methylpropyl, 2-bromo-2-methylpropyl, 3-fluoro-2-methylpropyl, 3-chloro-2-methylpropyl, 2,3-dichloro-2-methylpropyl, 3-bromo-2,2-dimethylpropyl, 3-chloro-2,2-dimethylpropyl, 3-fluoro-2,2-dimethylpropyl, 2,3-dichloro-1,2-dimethylpropyl, 1,2-dimethyl-2-fluoroethyl, 1,2-dimethyl-2-chloroethyl, 1,2-dimethyl-2-bromoethyl, 3-fluoro-1,2-dimethylpropyl, 3-chloro-1,2-dimethylpropyl, 3,3-difluoro-1,2-dimethylpropyl, 3,3,3-trifluoro-2-trifluoromethyl-2-methylpropyl, 1-dichloromethyl-2-methylpropyl, 1-trifluoromethyl-2-methylpropyl, 1-dichloromethyl-2-methylpropyl, 2,2-dimethyl-1-trichloromethylpropyl, 2,2-dimethyl-1-dichloromethylpropyl, 3-fluoro-1,3-dimethylbutyl, 3-chloro-1,3-dimethylbutyl, 3-bromo-1,3-dimethylbutyl, 3-fluoro-2,3-dimethylbutyl, 3-chloro-2,3-dimethylbutyl, 3-bromo-2,3-dimethylbutyl, 3-fluoro-1,2,2-trimethylpropyl, 3-chloro-1,2,2-trimethylpropyl, 3-bromo-1,2,2-trimethylpropyl, 2-fluoro-1-ethyl-2-methylpropyl, 2-bromo-1-ethyl-2-methylpropyl, 2-chloro-1-ethyl-2-methylpropyl, 2-methyl-2-methoxypropyl, 1,2-dimethyl-2-methoxypropyl, 2,2-dichloro-2-fluoro-1-methylethyl, or 2-methyl-1-trichloromethylpropyl.

The compounds of formula (1) wherein $R^1$ is 1-methyl-2-butynyl; $R^2$ is hydrogen; and $R^3$ is any of the following substituents:
isobutyl, 1,2-dimethylpropyl, isopentyl, neopentyl, 1,2,2-trimethylpropyl, 1-ethyl-2-methylpropyl, 3,3-dimethylbutyl, 1,3-dimethylbutyl, 1-ethyl-2,2-dimethylpropyl, 1-methyl-2,2,2-trichloroethyl, 1-methyl-2,2-dichloroethyl, 1-methyl-2,2-difluoroethyl, 1-methyl-2-chloropropyl, 1-methyl-2,2-dichloropropyl, 1-methyl-2,2-difluoropropyl, 2-chloro-2-methylpropyl, 2-fluoro-2-methylpropyl, 2-bromo-2-methylpropyl, 3-fluoro-2-methylpropyl, 3-chloro-2-methylpropyl, 2,3-dichloro-2-methylpropyl, 3-bromo-2,2-dimethylpropyl, 3-chloro-2,2-dimethylpropyl, 3-fluoro-2,2-dimethylpropyl, 2,3-dichloro-1,2-dimethylpropyl, 1,2-dimethyl-2-fluoroethyl, 1,2-dimethyl-2-chloroethyl, 1,2-dimethyl-2-bromoethyl, 3-fluoro-1,2-dimethylpropyl, 3-chloro-1,2-dimethylpropyl, 3,3-difluoro-1,2-dimethylpropyl, 1-dichloromethyl-2-methylpropyl, 1-dichloromethyl-2-methylpropyl, 2,2-dimethyl-1-trichloromethyl, 2,2-dimethyl-1-dichloromethylpropyl, 3-fluoro-1,2,2-trimethylpropyl, 3-chloro-1,2,2-trimethylpropyl, 2-fluoro-1-ethyl-2-methylpropyl, 2-bromo-1-ethyl-2-methylpropyl, 2-chloro-1-ethyl-2-methylpropyl, 2-methyl-2-methyloxypropyl, 1,2-dimethyl-2-methyloxypropyl, 2,2-dichloro-2-fluoro-1-methylethyl, or 2-methyl-1-trichloromethylpropyl.

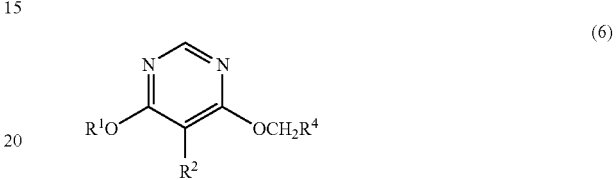

(6)

The compounds of formula (6) wherein $R^1$ is 2-propynyl; $R^2$ is hydrogen; and $R^4$ is any of the following substituents:
cyclopropyl, 1-methylcyclopropyl, 2-methylcyclopropyl, 2-fluorocyclopropyl, 2-chlorocyclopropyl, 1,2-dimethylcyclopropyl, 2,2-dimethylcyclopropyl, 2,2-dichloro-1-methylcyclopropyl, 2,2-dichloro-3,3-dimethylcyclopropyl, cyclobutyl, 1-methylcyclobutyl, 2-methylcyclobutyl, 1-chlorocyclobutyl, 2-chlorocyclobutyl, cyclopentyl, 1-methylcyclopentyl, 2-methylcyclopentyl, 2-chlorocyclopentyl, cyclohexyl, 2,2-difluorocyclobutyl, or 1,2-dimethylcyclopentyl.

The compounds of formula (6) wherein $R^1$ is 2-butynyl; $R^2$ is hydrogen; and $R^4$ is any of the following substituents:
cyclopropyl, 1-methylcyclopropyl, 2-methylcyclopropyl, 2-fluorocyclopropyl, 2-chlorocyclopropyl, 1,2-dimethylcyclopropyl, 2,2-dimethylcyclopropyl, 2,2-dichloro-1-methylcyclopropyl, 2,2-dichloro-3,3-dimethylcyclopropyl, cyclobutyl, 1-methylcyclobutyl, 2-methylcyclobutyl, 1-chlorocyclobutyl, 2-chlorocyclobutyl, cyclopentyl, 1-methylcyclopentyl, 2-methylcyclopentyl, 2-chlorocyclopentyl, cyclohexyl, 2,2-difluorocyclobutyl, or 1,2-dimethylcyclopentyl.

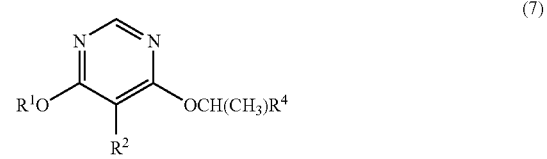

(7)

The compounds of formula (7) wherein $R^1$ is 2-propynyl; $R^2$ is hydrogen; and $R^4$ is any of the following substituents:
cyclopropyl, 1-methylcyclopropyl, 2-methylcyclopropyl, 2-fluorocyclopropyl, 2-chlorocyclopropyl, 1,2-dimethylcyclopropyl, 2,2-dimethylcyclopropyl, 2,2-dichloro-1-methylcyclopropyl, 2,2-dichloro-3,3-dimethylcyclopropyl, cyclobutyl, 1-methylcyclobutyl, 2-methylcyclobutyl, 1-chlorocyclobutyl, 2-chlorocyclobutyl, cyclopentyl, 1-methylcyclopentyl, 2-methylcyclopentyl, 2-chlorocyclopentyl, cyclohexyl, 2,2-difluorocyclobutyl, or 1,2-dimethylcyclopentyl.

The compounds of formula (7) wherein $R^1$ is 2-butynyl; $R^2$ is hydrogen; and $R^4$ is any of the following substituents:

cyclopropyl, 1-methylcyclopropyl, 2-methylcyclopropyl, 2-fluorocyclopropyl, 2-chlorocyclopropyl, 1,2-dimethylcyclopropyl, 2,2-dimethylcyclopropyl, 2,2-dichloro-1-methylcyclopropyl, 2,2-dichloro-3,3-dimethylcyclopropyl, cyclobutyl, 1-methylcyclobutyl, 2-methylcyclobutyl, 1-chlorocyclobutyl, 2-chlorocyclobutyl, cyclopentyl, 1-methylcyclopentyl, 2-methylcyclopentyl, 2-chlorocyclopentyl, cyclohexyl, 2,2-difluorocyclobutyl, or 1,2-dimethylcyclopentyl.

The compounds of formula (7) wherein $R^1$ is 2-pentynyl; $R^2$ is hydrogen; and $R^4$ is any of the following substituents:

cyclopropyl, 1-methylcyclopropyl, 2-methylcyclopropyl, 2-fluorocyclopropyl, 2-chlorocyclopropyl, 1,2-dimethylcyclopropyl, 2,2-dimethylcyclopropyl, 2,2-dichloro-1-methylcyclopropyl, 2,2-dichloro-3,3-dimethylcyclopropyl, cyclobutyl, 1-methylcyclobutyl, 2-methylcyclobutyl, 1-chlorocyclobutyl, 2-chlorocyclobutyl, cyclopentyl, 1-methylcyclopentyl, 2-methylcyclopentyl, 2-chlorocyclopentyl, cyclohexyl, 2,2-difluorocyclobutyl, or 1,2-dimethylcyclopentyl.

The compounds of formula (7) wherein $R^1$ is 1-methyl-2-butynyl; $R^2$ is hydrogen; and $R^4$ is any of the following substituents:

cyclopropyl, 1-methylcyclopropyl, 2-methylcyclopropyl, 2-fluorocyclopropyl, 2-chlorocyclopropyl, 1,2-dimethylcyclopropyl, 2,2-dimethylcyclopropyl, 2,2-dichloro-1-methylcyclopropyl, 2,2-dichloro-3,3-dimethylcyclopropyl, cyclobutyl, 1-methylcyclobutyl, 2-methylcyclobutyl, 1-chlorocyclobutyl, 2-chlorocyclobutyl, cyclopentyl, 1-methylcyclopentyl, 2-methylcyclopentyl, 2-chlorocyclopentyl, cyclohexyl, 2,2-difluorocyclobutyl, or 1,2-dimethylcyclopentyl.

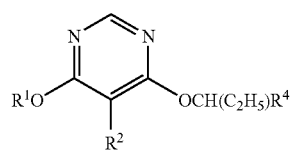

(8)

The compounds of formula (8) wherein $R^1$ is 2-propynyl; $R^2$ is hydrogen; and $R^4$ is any of the following substituents:

cyclopropyl, 1-methylcyclopropyl, 2-methylcyclopropyl, 2-fluorocyclopropyl, 2-chlorocyclopropyl, 1,2-dimethylcyclopropyl, 2,2-dimethylcyclopropyl, 2,2-dichloro-1-methylcyclopropyl, 2,2-dichloro-3,3-dimethylcyclopropyl, cyclobutyl, 1-methylcyclobutyl, 2-methylcyclobutyl, 1-chlorocyclobutyl, 2-chlorocyclobutyl, cyclopentyl, 1-methylcyclopentyl, 2-methylcyclopentyl, 2-chlorocyclopentyl, cyclohexyl, 2,2-difluorocyclobutyl, 1,2-dimethylcyclopentyl.

The compounds of formula (8) wherein $R^1$ is 2-butynyl; $R^2$ is hydrogen; and $R^4$ is any of the following substituents:

cyclopropyl, 1-methylcyclopropyl, 2-methylcyclopropyl, 2-fluorocyclopropyl, 2-chlorocyclopropyl, 1,2-dimethylcyclopropyl, 2,2-dimethylcyclopropyl, 2,2-dichloro-1-methylcyclopropyl, 2,2-dichloro-3,3-dimethylcyclopropyl, cyclobutyl, 1-methylcyclobutyl, 2-methylcyclobutyl, 1-chlorocyclobutyl, 2-chlorocyclobutyl, cyclopentyl, 1-methylcyclopentyl, 2-methylcyclopentyl, 2-chlorocyclopentyl, cyclohexyl, 2,2-difluorocyclobutyl, or 1,2-dimethylcyclopentyl.

The compounds of formula (8) wherein $R^1$ is 2-pentynyl; $R^2$ is hydrogen; and $R^4$ is any of the following substituents:

cyclopropyl, 1-methylcyclopropyl, 2-methylcyclopropyl, 2-fluorocyclopropyl, 2-chlorocyclopropyl, 1,2-dimethylcyclopropyl, 2,2-dimethylcyclopropyl, 2,2-dichloro-1-methylcyclopropyl, 2,2-dichloro-3,3-dimethylcyclopropyl, cyclobutyl, 1-methylcyclobutyl, 2-methylcyclobutyl, 1-chlorocyclobutyl, 2-chlorocyclobutyl, cyclopentyl, 1-methylcyclopentyl, 2-methylcyclopentyl, 2-chlorocyclopentyl, cyclohexyl, 2,2-difluorocyclobutyl, or 1,2-dimethylcyclopentyl.

The compounds of formula (8) wherein $R^1$ is 1-methyl-2-butynyl; $R^2$ is hydrogen; and $R^4$ is any of the following substituents:

cyclopropyl, 1-methylcyclopropyl, 2-methylcyclopropyl, 2-fluorocyclopropyl, 2-chlorocyclopropyl, 1,2-dimethylcyclopropyl, 2,2-dimethylcyclopropyl, 2,2-dichloro-1-methylcyclopropyl, 2,2-dichloro-3,3-dimethylcyclopropyl, cyclobutyl, 1-methylcyclobutyl, 2-methylcyclobutyl, 1-chlorocyclobutyl, 2-chlorocyclobutyl, cyclopentyl, 1-methylcyclopentyl, 2-methylcyclopentyl, 2-chlorocyclopentyl, cyclohexyl, 2,2-difluorocyclobutyl, or 1,2-dimethylcyclopentyl.

The pests against which the present compound has activity may include, for example, arthropods such as insects and acarines; and nemathelminthes such as nematodes. Specific examples are listed below:

Hemiptera:
Delphacidae such as *Laodelphax striatellus, Nilaparvata lugens*, and *Sogatella furcifera;*
Deltocephalidae such as *Nephotettix cincticeps* and *Empoasca onukii;*
Aphididae such as *Aphis gossypii* and *Myzus persicae;*
Pentatomidae;
Aleyrodidae such as *Trialeurodes vaporariorum, Bemisia tabaci*, and *Bemisia argentifolii;*
Coccidae;
Tingidae;
Psyllidae;
Lepidoptera:
Pyralidae such as *Chilo suppressalis, Cnaphalocrocis medinalis, Ostrinia nubilalis*, and *Parapediasia tererrella;*
Noctuidae such as *Spodoptera litura, Spodoptera exigua, Pseudaletia separata, Mamestra brassicae, Agrotis ipsilon, Thoricoplusia* spp., *Heliothis* spp., *Helicoverpa* spp., and *Earias* spp.;
Pieridae such as *Pieris rapae crucivora;*
Tortricidae such as *Adoxophyes orana fasciata, Grapholita molesta*, and *Cydia pomonella;*
Carposinidae such as *Carposina niponensis;*
Lyonetiidae such as *Lyonetia clerkella;*
Gracillariidae such as *Phyllonorycter ringoniella;*
Phyllocnistidae such as *Phyllocnistis citrella;*
Yponomeutidae such as *Plutela xylostella;*
Gelechiidae such as *Pectinophora gossypiella;*
Arctiidae;
Tineidae;
Diptera:
Calicidae such as *Culex pipiens pallens, Culex tritaeniorhynchus*, and *Culex quinquefasciatus;*
*Aedes* spp. such as *Aedes aegypti* and *Aedes albopictus;*
*Anopheles* spp. such as *Anopheles sinensis;*
Chironomidae;
Muscidae such as *Musca domestica* and *Muscina stabulans;*
Calliphoridae;
Sarcophagidae;
Fanniidae;
Anthomyiidae such as *Delia platura* and *Delia antiqua;*

Tephritidae;
Drosophilidae;
Psychodidae;
Tabanidae;
Simuliidae;
Stomoxyidae;
Agromyzidae;
Coleoptera:
*Diabrotica* spp. such as *Diabrotica virgifera virgifera* and *Diabrotica undecimpunctata howardi;*
Scarabaeidae such as *Anomala cuprea* and *Anomala rufocuprea;*
Curculionidae such as *Sitophilus zeamais, Lissorhoptrus oryzophilus,* and *Callosohruchuys chienensis;*
Tenebrionidae such as *Tenebrio molitor* and *Tribolium castaneum;*
Chrysomelidae such as *Oulema oryzae, Aulacophora femoralis, Phyllotreta striolata,* and *Leptinotarsa decemlineata;*
Anobiidae;
*Epilachna* spp. such as *Epilachna vigintioctopunctata;*
Lyctidae;
Bostrychidae;
Cerambycidae;
*Paederus fuscipes;*
Thysanoptera:
Thripidae spp. including *Thrips* spp. such as *Thrips palmi, Frankliniella* spp. such as *Frankliniella occidentalis,* and *Sciltothrips* spp. such as *Sciltothrips dorsalis;*
Phlaeothripidae spp.;
Hymenoptera:
Tenthredinidae;
Formicidae;
Vespidae;
Dictyoptera:
*Periplaneta* spp.;
*Blatta* spp.;
Orthoptera:
Acrididae;
Gryllotalpidae;
Aphaniptera:
*Pulex irritans;*
Anoplura:
*Pediculus humanus;*
Isoptera:
Termitidae;
Acarina:
Tetranychidae such as *Tetranychus urticae, Tetranychus kanzawai, Panonychus citri, Panonychus ulmi,* and *Oligonychus* spp.;
Eriophyidae such as *Aculops pelekassi* and *Aculus schlechtendali;*
Tarsonemidae such as *Polyphagotarsonemus latus;*
Tenuipalpidae;
Tuckerellidae;
Ixodidae such as *Haemaphysalis longicornis, Haemaphysalis flava, Dermacentor taiwanicus, Ixodes ovatus, Ixodes persulcatus,* and *Boophilus microplus;*
Acaridae such as *Tyrophagus putrescentiae;*
Epidermoptidae such as *Dermatophagoides farinae* and *Dermatophagoides ptrenyssnus;*
Cheyletidae such as *Cheyletus eruditus, Cheyletus malaccensis,* and *Cheyletus moorei;*
Dermanyssidae;
Nematoda:
*Pratylenchus coffeae, Pratylenchus fallax, Heterodera glycines, Globodera rostochiensis, Meloidogyne hapla, Meloidogyne incognita.*

The pesticidal composition of the present invention is comprising the present compound as an active ingredient, and an additive. The pesticidal composition of the present invention may be prepared by mixing the present compound with a solid carrier, a liquid carrier, a gaseous carrier and/or a bait, and if necessary, adding a surfactant and other adjuvants, and then formulating the mixture into an oil solution, an emulsifiable concentrate, a flowable, a granule, a dust, a poison bait, a microcapsule formulation, or the like. In each of these formulations, the present compound is usually contained in an amount of 0.1% to 95% by weight.

The solid carrier which can be used in the formulation may include, for example, the following materials in fine powder or granular form: clays (e.g., kaolin clay, diatomaceous earth, synthetic hydrated silicon oxide, bentonite, Fubasami clay, acid clay); talc, ceramic, and other inorganic minerals (e.g., sericite, quartz, sulfur, activated carbon, calcium carbonate, hydrated silica); and chemical fertilizers (e.g., ammonium sulfate, ammonium phosphate, ammonium nitrate, urea, ammonium chloride).

The liquid carrier may include, for example, water; alcohols (e.g., methanol, ethanol); ketones (e.g., acetone, methyl ethyl ketone); aromatic hydrocarbons (e.g., benzene, toluene, xylene, ethylbenzene, methylnaphthalene); aliphatic hydrocarbons (e.g., hexane, cyclohexane, kerosine, light oil); esters (e.g., ethyl acetate, butyl acetate); nitriles (acetonitrile, isobutyronitrile); ethers (e.g., diisopropyl ether, dioxane); acid amides (e.g., N,N-dimethylformamide, N,N-dimethylacetamide); halogenated hydrocarbons (e.g., dichloromethane, trichloroethane, carbon tetrachloride); dimethylsulfoxide; and vegetable oils (e.g., soy bean oil and cotton seed oil).

The gaseous carrier may include, for example, fluorocarbon, butane gas, liquefied petroleum gas (LPG), dimethyl ether, and carbon dioxide.

The surfactant may include, for example, alkyl sulfate salts; alkylsulfonic acid salts; alkylarylsulfonic acid salts; alkyl aryl ethers and their polyoxyethylene derivatives; polyethylene glycol ethers; polyhydric alcohol esters; and sugar alcohol derivatives.

The other adjuvants may include binders, dispersants, and stabilizers, specific examples of which are casein, gelatin, polysaccharides (e.g., starch, gum arabic, cellulose derivatives, alginic acid), lignin derivatives, bentonite, sugars, synthetic water-soluble polymers (e.g., polyvinyl alcohol, polyvinylpyrrolidone, polyacrylic acid), PAP (isopropyl acid phosphate), BHT (2,6-di-t-butyl-4-methylphenol), BHA (mixtures of 2-t-butyl-4-methoxyphenol and 3-t-butyl-4-methoxyphenol), vegetable oils, mineral oils, fatty acids, and fatty acid esters.

The base material for poison baits may include, for example, bait ingredients such as grain powders, vegetable oils, sugars, and crystalline cellulose; antioxidants such as dibutylhydroxytoluene and nordihydroguaiaretic acid; preservatives such as dehydroacetic acid; agents for preventing children and pets from erroneously eating, such as hot pepper powder; and pest-attractive flavors such as cheese flavor, onion flavor, and peanut oil.

The method for controlling pests according to the present invention is carried out by applying the pesticidal composition of the present invention to pests or habitats of pests.

When the pesticidal composition of the present invention is used for the control of pests in agriculture and forestry, the application amount is usually 1 to 10,000 g as the amount of the present compound per 1,000 m². Formulations such as emulsifiable concentrates, wettable powders, flowables, and microcapsule formulations are usually used after dilution with water to have an active ingredient concentration of 10 to 10,000 ppm, while formulations such as granules and dusts are usually used as such.

The pesticidal composition of the present invention can be used by foliar treatment to plants such as crop plants to be protected from pests or can also be used by treatment to seedbeds prior to the planting of crop plant seedlings or to planting holes or plant bottoms in the planting. Further, for the purpose of controlling pests inhabiting the soil of a cultivated land, the pesticidal composition of the present invention may also be used by treatment to the soil. The pesticidal composition of the present invention can also be used by winding a resin formulation processed into a sheet, string, or cord form around crop plants, or by stretching it in the vicinity of crop plants and/or laying it on the soil surface at the plant bottom.

The pesticidal composition of the present invention can also be used in admixture or combination with other insecticides, nematocides, acaricides, bactericides, fungicides, herbicides, plant growth regulators, synergists, fertilizers, soil conditioners, animal feeds, and the like.

The insecticide and/or acaricide and/or nematocide which can be used may include, for example, organophosphorus compounds such as Fenitrothion, Fenthion, Pyridaphenthion, Diazinon, Chlorpyriphos, Chlorpyriphos-methyl, Acephate, Methidathion, Disulfoton, DDVP, Sulprofos, Profenofos, Cyanophos, Dioxabenzofos, Dimethoate, Phenthoate, Malathion, Trichlorfon, Azinphos-methyl, Monocrotophos, Dicrotophos, Ethion, and Fosthiazate; carbamate compounds such as BPMC, Benfuracarb, Propoxur, Carbosulfan, Carbaril, Methomyl, Ethiofencarb, Aldicarb, Oxamyl, Fenothiocarb, Thiodicarb, and Alanycarb; pyrethroid compounds such as Etofenprox, Fenvalerate, Esfenvalerate, Fenpropathrin, Cypermethrin, α-Cypermethrin, Z-Cypermethrin, Permethrin, Cyhalothrin, λ-Cyhalothrin, Cyfluthrin, β-Cyfluthrin, Deltamethrin, Cycloprothrin, τ-Fluvalinate, Flucythrinate, Bifenthrin, Acrinathrin, Traromethrin, Silafluofen, and Halfenprox; neonicotinoid compounds such as Thiamethoxiam and Acetamiprid; benzoylphenylurea compounds such as Chlorfluazuron, Teflubenzuron, Fulphenoxron, and Lufenuron; benzoylhydrazide compounds such as Tebufenozide, Halofenozide, Methoxyfenozide, and Chromafenozide; thiadiazine derivatives such as Buprofezin; Nereistoxin derivatives such as Cartap, Thiocyclam, and Bensultap; chlorinated hydrocarbon compounds such as Endosulfan, γ-BHC, and 1,1-bis(chlorophenyl)-2,2,2-trichloroethanol; formamidine derivatives such as Amitraz and Chlordimeform; thiourea derivatives such as Diafenthiuron; phenylpyrazol compounds; Chlorfenapyr; Pymetrozine; Spinosad; Indoxa carb; Pyridalyl; Pyriproxyfen; Fenoxycarb; Diofenolan; Cyromazine; Bromopropylate; Tetradifon; Chinomethionat; Propargite; Fenbutatin oxide; Hexathiazox; Etoxazole; Clofentezine; Pyridaben; Fenpyroximate; Tebufenpyrad; Pyrimidifen; Fenazaquin; Acequinocyl; Bifenazate; Fluacrypyrim; Milbemectin; Avermectin; Emamectin benzoate; Azadilactin [AZAD]; and polynactin complexes [e.g., tetranactin, dinactin, trinactin].

EXAMPLES

The present invention will be further illustrated by the following production examples, formulation examples, and test examples; however, the present invention is not limited to these examples.

In the production examples and reference production examples, all $^1$H-NMR data were measured in deuterated chloroform using tetramethylsilane as the internal standard, unless otherwise indicated.

The following will describe production examples for the present compounds. The present compound numbers used in the production examples are those shown below in Tables 1 and 2.

Production Example 1

In 0.5 ml of tetrahydrofuran was suspended 0.02 g of sodium hydride (60% in oil), to which 0.1 ml of a solution containing 0.02 g of 2-butyn-1-ol in tetrahydrofuran was added dropwise at room temperature. After stirring at room temperature for 20 minutes, 0.1 ml of a solution containing 0.05 g of 4-chloro-6-(isopropyloxy)pyrimidine in tetrahydrofuran was added dropwise at room temperature, followed by stirring for 2 hours. The mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.05 g of 4-(2-butynyloxy)-6-isopropoxypyrimidine (the present compound (1)).

$^1$H-NMR: 1.34 (d, 6H), 1.87 (t, 3H), 4.94 (q, 2H), 5.25–5.34 (m, 1H), 6.05 (s, 1H), 8.42 (s, 1H).

Production Example 2

In 4 ml of tetrahydrofuran was suspended 0.11 g of sodium hydride (60% in oil), to which 0.5 ml of a solution containing 0.19 g of 1-cyclopropylethanol in tetrahydrofuran was added dropwise at room temperature. After stirring at room temperature for 10 minutes, 0.5 ml of a solution containing 0.3 g of 4,6-dichloropyrimidine in tetrahydrofuran was added dropwise at 0° C., followed by stirring at the same temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated to give a crude product of 4-chloro-6-(1-cyclopropylethoxy)pyrimidine.

In 4 ml of tetrahydrofuran was suspended 0.11 g of sodium hydride (60% in oil), to which 0.5 ml of a solution containing 0.15 g of 2-butyn-1-ol in tetrahydrofuran was added dropwise at room temperature, followed by stirring for 10 minutes. To this was slowly added dropwise 0.5 ml of a solution containing the above 4-chloro-6-(1-cyclopropylethoxy)pyrimidine in tetrahydrofuran, followed by stirring at room temperature for 1 hour. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The resulting residue was subjected to silica gel column chromatography to give 0.22 g of 4-(2-butynyloxy)-6-(1-cyclopropylethoxy)pyrimidine (the present compound (2)).

$^1$H-NMR: 0.28–0.33 (m, 1H), 0.39–0.58 (m, 3H), 1.08–1.14 (m, 1H), 1.38 (d, 3H), 1.87 (t, 3H), 4.65–4.74 (m, 1H), 4.94 (q, 2H), 6.08 (s, 1H), 8.39 (s, 1H)

Production Example 3

In 2 ml of tetrahydrofuran was suspended 0.06 g of sodium hydride (60% in oil), to which 0.3 ml of a solution containing 0.09 g of 2-butyn-1-ol in tetrahydrofuran was added dropwise at room temperature, followed by stirring for 10 minutes. To this was added dropwise 0.3 ml of a solution containing 0.24 g of 4-chloro-6-(1,2,2-trimethylpropyloxy)pyrimidine in tetrahydrofuran at room temperature, followed by stirring for 3 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.25 g of 4-(2-butynyloxy)-6-(1,2,2-trimethylpropyloxy)pyrimidine (the present compound (3)).

$^1$H-NMR: 0.96 (s, 9H), 1.22 (d, 3H), 1.87 (t, 3H), 4.93–5.01 (m, 3H, involving two quartet at 4.95 and 4.98), 6.06 (s, 1H), 8.42 (s, 1H).

Production Example 4

In 3 ml of tetrahydrofuran was suspended 0.08 g of sodium hydride (60% in oil), to which 0.3 ml of a solution containing 0.12 g of 2-butyn-1-ol in tetrahydrofuran was added dropwise at room temperature, followed by stirring for 10 minutes. To this was added dropwise 0.3 ml of a solution containing 0.35 g of 4-chloro-6-(1-ethyl-2,2-dimethylpropyloxy)pyrimidine in tetrahydrofuran at room temperature, followed by stirring for 6 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.22 g of 4-(2-butynyloxy)-6-(1-ethyl-2,2-dimethylpropyloxy)pyrimidine (the present compound (4)).

$^1$H-NMR: 0.84 (t, 3H), 0.92 (s, 9H), 1.52–1.72 (m, 2H), 1.88 (t, 3H), 4.95 (q, 2H), 5.13 (dd, 1H), 6.07 (s, 1H), 8.39 (s, 1H).

Production Example 5

In 4 ml of tetrahydrofuran was suspended 0.11 g of sodium hydride (60% in oil), to which 0.5 ml of a solution containing 0.23 g of 4-methyl-2-pentanol in tetrahydrofuran was added dropwise at room temperature, followed by stirring for 10 minutes. To this was added dropwise 0.5 ml of a solution containing 0.3 g of 4,6-dichloropyrimidine in tetrahydrofuran at 0° C., followed by stirring at the same temperature for 2 hours and further stirring at room temperature for 4 hours. The reaction mixture was then poured into a saturated aqueous ammonium chloride solution, which was extracted three times with t-butyl methyl ether. The combined organic layers were washed with a saturated aqueous sodium chloride solution and dried over anhydrous magnesium sulfate to give a crude product of 4-chloro-6-(1,3-dimethylbutoxy)pyrimidine.

In 3.5 ml of tetrahydrofuran was suspended 0.1 g of sodium hydride (60% in oil), to which 0.3 ml of a solution containing 0.16 g of 2-butyn-1-ol in tetrahydrofuran was added dropwise at room temperature, followed by stirring for 10 minutes. To this was added dropwise 0.3 ml of a solution containing the above 4-chloro-6-(1,3-dimethylbutoxy)pyrimidine in tetrahydrofuran, followed by stirring at room temperature for 4 hour. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The resulting residue was subjected to silica gel column chromatography to give 0.30 g of 4-(2-butynyloxy)-6-(1,3-dimethylbutyloxy)pyrimidine (the present compound (5)).

$^1$H-NMR: 0.89–0.94 (m, 6H), 1.29 (d, 3H), 1.32–1.41 (m, 1H), 1.65–1.83 (m, 2H), 1.87 (t, 3H), 4.94 (q, 2H), 5.26–5.35 (m, 1H), 6.05 (s, 1H), 8.42 (s, 1H).

Production Example 6

In 1.6 ml of tetrahydrofuran was suspended 0.04 g of sodium hydride (60% in oil), to which 0.2 ml of a solution containing 0.06 g of 2-butyn-1-ol in tetrahydrofuran was added dropwise at room temperature, followed by stirring for 10 minutes. To this was added dropwise 0.2 ml of a solution containing 0.16 g of 4-chloro-6-(2,2-dimethylpropyloxy)pyrimidine in tetrahydrofuran at room temperature, followed by stirring for 2 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.15 g of 4-(2-butynyloxy)-6-(2,2-dimethylpropyloxy)pyrimidine (the present compound (6)).

$^1$H-NMR: 1.01 (s, 9H), 1.87 (t, 3H), 3.98 (s, 2H), 4.95 (q, 2H), 6.11 (s, 1H), 8.43 (s, 1H).

Production Example 7

In 4 ml of tetrahydrofuran was suspended 0.11 g of sodium hydride (60% in oil), to which 0.5 ml of a solution containing 0.24 g of 4,4-dimethyl-2-pentanol in tetrahydrofuran was added dropwise at room temperature, followed by stirring for 10 minutes. To this was added dropwise 0.5 ml of a solution containing 0.3 g of 4,6-dichloropyrimidine in tetrahydrofuran at 0° C., followed by stirring at the same temperature for 2 hours and further stirring at room temperature for 4 hours. The reaction mixture was then poured into a saturated aqueous ammonium chloride solution, which was extracted three times with t-butyl methyl ether. The combined organic layers were washed with a saturated aqueous sodium chloride solution and dried over anhydrous magnesium sulfate to give a crude product of 4-chloro-6-(1,3,3-trimethylbutoxy)pyrimidine.

In 2 ml of tetrahydrofuran was suspended 0.03 g of sodium hydride (60% in oil), to which 0.5 ml of a solution containing 0.05 g of 2-butyn-1-ol in tetrahydrofuran was added dropwise at room temperature, followed by stirring for 10 minutes. To this was added dropwise 0.5 ml of a solution containing the above 4-chloro-6-(1,3,3-trimethylbutoxy)pyrimidine in tetrahydrofuran, followed by stirring at room temperature for 4 hour. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.14 g of 4-(2-butynyloxy)-6-(1,3,3-trimethylbutyloxy)pyrimidine (the present compound (7)).

$^1$H-NMR: 0.91 (s, 9H), 1.29 (d, 3H), 1.40 (dd, 1H), 1.78 (dd, 1H), 1.87 (t, 3H), 4.94 (q, 2H), 5.34–5.39 (m, 1H), 6.03 (s, 1H), 8.44 (s, 1H).

Production Example 8

In 2 ml of tetrahydrofuran was suspended 0.03 g of sodium hydride (60% in oil), to which 0.3 ml of a solution containing 0.05 g of 2-butyn-1-ol in tetrahydrofuran was added dropwise at room temperature, followed by stirring for 10 minutes. To this was added dropwise 0.3 ml of a solution containing 0.10 g of 4-chloro-6-[1-(1-methylcyclopropyl)ethyloxy]pyrimidine in tetrahydrofuran at room temperature for 3 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.09 g of 4-(2-butynyloxy)-6-[1-(1-methylcyclopropyl)ethyloxy]pyrimidine (the present compound (8)).

$^1$H-NMR: 0.29–0.37 (m, 2H), 0.43–0.46 (m, 1H), 0.55–0.61 (m, 1H), 1.14 (s, 3H), 1.33 (d, 3H), 1.87 (t, 3H), 4.71 (q, 1H), 4.94 (q, 2H), 6.07 (s, 1H), 8.39 (s, 1H).

Production Example 9

In 4 ml of tetrahydrofuran was suspended 0.11 g of sodium hydride (60% in oil), to which 0.5 ml of a solution containing 0.44 g of 2,2-bis(trifluoromethyl)propanol in tetrahydrofuran was added dropwise at room temperature, followed by stirring for 10 minutes. To this was added dropwise 0.5 ml of a solution containing 0.3 g of 4,6-dichloropyrimidine in tetrahydrofuran at 0° C., followed by stirring at the same temperature for 1.5 hours. The reaction mixture was then poured into a saturated aqueous ammonium chloride solution, which was extracted three times with t-butyl methyl ether. The combined organic layers were washed with a saturated aqueous sodium chloride solution and dried over anhydrous magnesium sulfate to give a crude product of 4-chloro-6-[2,2-bis(trifluoromethyl)propoxy]pyrimidine.

In 4 ml of tetrahydrofuran was suspended 0.11 g of sodium hydride (60% in oil), to which 0.5 ml of a solution containing 0.16 g of 2-butyn-1-ol in tetrahydrofuran was added dropwise at room temperature, followed by stirring for 10 minutes. To this was added dropwise 0.5 ml of a solution containing the above 4-chloro-6-[2,2-bis(trifluoromethyl)propoxy]pyrimidine in tetrahydrofuran, followed by stirring at room temperature for 6 hour. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.30 g of 4-(2-butynyloxy)-6-[2,2-bis(trifluoromethyl)propyloxy]pyrimidine (the present compound (9)).

$^1$H-NMR: 1.49 (s, 3H), 1.87 (t, 3H), 4.69 (s, 2H), 4.97 (q, 2H), 6.17 (s, 1H), 8.45 (s, 1H).

Production Example 10

In 5 ml of tetrahydrofuran was suspended 0.14 g of sodium hydride (60% in oil), to which 0.5 ml of a solution containing 0.22 g of 2-butyn-1-ol in tetrahydrofuran was added dropwise at room temperature, followed by stirring for 10 minutes. To this was added dropwise 0.5 ml of a solution containing 0.62 g of 4-chloro-6-(3-chloro-2,2-dimethylpropyloxy)pyrimidine in tetrahydrofuran at 0° C., followed by stirring at the same temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.62 g of 4-(2-butynyloxy)-6-(3-chloro-2,2-dimethylpropyloxy)pyrimidine (the present compound (10)).

$^1$H-NMR: 1.11 (s, 6H), 1.87 (t, 3H), 3.52 (s, 2H), 4.16 (s, 2H), 4.96 (q, 2H), 6.11 (s, 1H), 8.44 (s, 1H).

Production Example 11

In 4 ml of tetrahydrofuran was suspended 0.10 g of sodium hydride (60% in oil), to which 0.5 ml of a solution containing 0.15 g of 2-butyn-1-ol in tetrahydrofuran was added dropwise at room temperature, followed by stirring for 10 minutes. To this was added dropwise 0.5 ml of a solution containing 0.41 g of 4-chloro-6-(3,3-dimethylbutyloxy)pyrimidine in tetrahydrofuran at 0° C., followed by stirring at the same temperature for 5 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.40 g of 4-(2-butynyloxy)-6-(3,3-dimethylbutyloxy)pyrimidine (the present compound (11)).

$^1$H-NMR: 0.98 (s, 9H), 1.70 (t, 2H), 1.87 (t, 3H), 4.37 (t, 2H), 4.95 (q, 2H), 6.08 (s, 1H), 8.44 (s, 1H).

Production Example 12

In 3.5 ml of tetrahydrofuran was suspended 0.09 g of sodium hydride (60% in oil), to which 0.5 ml of a solution containing 0.13 g of 2-butyn-1-ol in tetrahydrofuran was added dropwise at room temperature, followed by stirring for 10 minutes. To this was added dropwise 0.5 ml of a solution containing 0.35 g of 4-chloro-6-(1,2-dimethylpropyloxy)pyrimidine in tetrahydrofuran at 0° C., followed by stirring at the same temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.41 g of 4-(2-butynyloxy)-6-(1,2-dimethylpropyloxy)pyrimidine (the present compound (12)).

$^1$H-NMR: 0.94 (d, 3H), 0.96 (d, 3H), 1.25 (d, 3H), 1.87–1.98 (m, 4H, involving a triplet at 1.87), 4.94–5.06 (m, 3H, involving a quartet at 4.95), 6.06 (s, 1H), 8.42 (s, 1H).

Production Example 13

In 4 ml of tetrahydrofuran was suspended 0.11 g of sodium hydride (60% in oil), to which 0.5 ml of a solution containing 0.16 g of 2-butyn-1-ol in tetrahydrofuran was added dropwise at room temperature, followed by stirring for 10 minutes. To this was added dropwise 0.5 ml of a solution containing 0.56 g of 4-chloro-6-(3-bromo-2,2-dimethylpropyloxy)pyrimidine in tetrahydrofuran at 0° C., followed by stirring at the same temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.54 g of 4-(2-butynyloxy)-6-(3-bromo-2,2-dimethylpropyloxy)pyrimidine (the present compound (13)).

$^1$H-NMR: 1.14 (s, 6H), 1.87 (t, 3H), 3.45 (s, 2H), 4.16 (s, 2H), 4.96 (q, 2H), 6.11 (s, 1H), 8.44 (s, 1H).

Production Example 14

First, 0.41 g of 4-(2-butynyloxy)-6-(2-hydroxy-1,2-dimethylpropyloxy)pyrimidine was dissolved in 3 ml of chloroform, to which 0.5 ml of a solution containing 0.31 g of dimethylaminosulfate trifluoride (hereinafter referred to as DAST) in chloroform was added dropwise at 0° C., followed by stirring for 20 minutes. The reaction mixture was then poured into water, which was extracted three times with chloroform. The combined organic layers were washed with a saturated aqueous sodium chloride solution, dried over anhydrous magnesium sulfate, and then concentrated. The residue was subjected to silica gel column chromatography to give 0.20 g of 4-(2-butynyloxy)-6-(2-fluoro-1,2-dimethylpropyloxy)pyrimidine (the present compound (14)).

$^1$H-NMR: 1.32 (d, 3H), 1.37 (d, 3H), 1.43 (d, 3H), 1.87 (t, 3H), 4.95 (q, 2H), 5.33 (dq, 1H), 6.12 (s, 1H), 8.43 (s, 1H).

Production Example 15

In 4 ml of tetrahydrofuran was suspended 0.11 g of sodium hydride (60% in oil), to which 0.4 ml of a solution containing 0.15 g of 2-methyl-1-propanol in tetrahydrofuran was added dropwise at 0° C., followed by stirring for 10 minutes. To this was added dropwise 0.4 ml of a solution containing 0.30 g of 4,6-dichloropyrimidine in tetrahydrofuran, followed by stirring at the same temperature for 2 hours. To this was added dropwise 0.4 ml of a solution containing 0.14 g of 2-butyn-1-ol at 0° C. and further added 0.11 g of sodium hydride (60% in oil), followed by further stirring at room temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.35 g of 4-(2-butynyloxy)-6-isobutyloxypyrimidine (the present compound (15)).

$^1$H-NMR: 1.00 (d, 6H), 1.87 (t, 3H), 2.01–2.12 (m, 1H), 4.07 (d, 2H), 4.95 (q, 2H), 6.10 (s, 1H), 8.43 (s, 1H).

Production Example 16

In 4 ml of tetrahydrofuran was suspended 0.10 g of sodium hydride (60% in oil), to which 0.4 ml of a solution containing 0.21 g of 3-methyl-2-pentanol in tetrahydrofuran was added dropwise at 0° C., followed by stirring for 10 minutes. To this was slowly added dropwise 0.4 ml of a solution containing 0.30 g of 4,6-dichloropyrimidine in tetrahydrofuran, followed by stirring at the same temperature for 3 hours. To this was added dropwise 0.4 ml of a solution containing 0.14 g of 2-butyn-1-ol at 0° C. and further added 0.10 g of sodium hydride (60% in oil), followed by further stirring at room temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.29 g of 4-(2-butynyloxy)-6-(1,2-dimethylbutyloxy)pyrimidine (the present compound (16)).

$^1$H-NMR: 0.86–0.97 (m, 6H), 1.14–1.27 (m, 4H), 1.47–1.82 (m, 2H), 1.87 (t, 3H), 4.95 (q, 2H), 5.08–5.17 (m, 1H), 6.05 (s, 1H), 8.42 (s, 1H).

Production Example 17

First, 0.31 g of 4-(2-pentynyloxy)-6-(2-hydroxy-1,2-dimethylpropyloxy)pyrimidine was dissolved in 3 ml of chloroform, to which 0.5 ml of a solution containing 0.24 g of DAST in chloroform was added dropwise at 0° C., followed by stirring for 10 minutes. The reaction mixture was then poured into water, which was extracted three times with chloroform. The combined organic layers were washed with a saturated aqueous sodium chloride solution, dried over anhydrous magnesium sulfate, and then concentrated. The residue was subjected to silica gel column chromatography to give 0.16 g of 4-(2-fluoro-1,2-dimethylpropyloxy)-6-(2-pentynyloxy)pyrimidine (the present compound (17)).

$^1$H-NMR: 1.14 (t, 3H), 1.33 (d, 3H), 1.37 (d, 3H), 1.44 (d, 3H), 2.22 (qt, 2H), 4.97 (t, 2H), 5.27–5.38 (m, 1H), 6.12 (s, 1H), 8.42 (s, 1H).

Production Example 18

In 1.5 ml of tetrahydrofuran was suspended 0.04 g of sodium hydride (60% in oil), to which 0.3 ml of a solution containing 0.05 g of 2-butyn-1-ol in tetrahydrofuran was added dropwise at room temperature, followed by stirring for 10 minutes. To this was added dropwise 0.3 ml of a solution containing 0.16 g of 4-chloro-6-(2,2-dimethoxy-1-methylethoxy)pyrimidine in tetrahydrofuran at 0° C., followed by stirring at the same temperature for 1 hour and further stirring at room temperature for 3 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.11 g of 4-(2-butynyloxy)-6-(2,2-dimethoxy-1-methylethoxy)pyrimidine (the present compound (18)).

$^1$H-NMR: 1.32 (d, 3H), 1.87 (t, 3H), 3.42 (s, 3H), 3.45 (s, 3H), 4.40 (d, 1H), 4.94 (q, 2H), 5.36 (dt, 1H), 6.12 (s, 1H), 8.43 (s, 1H).

Production Example 19

In 4 ml of tetrahydrofuran was suspended 0.10 g of sodium hydride (60% in oil), to which 0.4 ml of a solution containing 0.33 g of 1,1,1-trichloro-2-propanol in tetrahydrofuran was added dropwise at 0° C., followed by stirring for 10 minutes. To this was added dropwise 0.4 ml of a solution containing 0.30 g of 4,6-dichloropyrimidine in tetrahydrofuran, followed by stirring at the same temperature for 35 minutes. To this was added dropwise 0.4 ml of a solution containing 0.16 g of 2-butyn-1-ol in tetrahydrofuran and further added 0.10 g of sodium hydride (60% in oil), followed by stirring at room temperature for 35 minutes. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.44 g of 4-(2-butynyloxy)-6-(2,2,2-trichloro-1-methylethoxy)pyrimidine (the present compound (19)).

$^1$H-NMR: 1.66 (d, 3H), 1.87 (t, 3H), 4.97 (q, 2H), 6.02 (q, 1H), 6.22 (s, 1H), 8.46 (s, 1H).

Production Example 20

In 1.2 ml of carbon tetrachloride were dissolved 0.15 g of 4-(2-butynylallyloxy)-6-(2-methylallyloxy)pyrimidine and 0.01 g of trioctylmethylammonium chloride, to which 1 ml of concentrated hydrochloric acid was added dropwise at 0° C., followed by stirring at 0° C. for 30 minutes and at room temperature for 50 minutes. The reaction mixture was then poured into water, which was extracted three times with t-butyl methyl ether. The combined organic layer was washed with a saturated aqueous sodium hydrogencarbonate solution, a saturated aqueous sodium chloride solution, dried over anhydrous magnesium, and then concentrated. The residue was subjected to silica gel column chromatography to give 0.08 g of 4-(2-butynyloxy)-6-(2-chloro-2-methylpropyloxy)pyrimidine (the present compound (20)).

$^1$H-NMR: 1.66 (s, 6H), 1.87 (t, 3H), 4.42 (s, 2H), 4.96 (q, 2H), 6.18 (s, 1H), 8.44 (s, 1H).

Production Example 21

In 3 ml of tetrahydrofuran was suspended 0.18 g of sodium hydride (60% in oil), to which 8.43 ml of a 0.4 M solution (tetrahydrofuran solution) of 1-cyclobutylethanol was added dropwise at 0° C., followed by stirring for 10 minutes. To this was added dropwise 0.3 ml of a solution containing 0.50 g of 4,6-dichloropyrimidine in tetrahydrofuran, followed by stirring at the same temperature for 3 hours. To this was added dropwise 0.3 ml of a solution containing 0.35 g of 2-butyn-1-ol in tetrahydrofuran and further added 0.24 g of sodium hydride (60% in oil), followed by stirring at room temperature for 7 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.45 g of 4-(2-butynyloxy)-6-(1-cylclobutylethyloxy)pyrimidine (the present compound (21)).

$^1$H-NMR: 0.94 (d, 3H), 0.96 (d, 3H), 1.15 (t, 3H), 1.25 (d, 3H), 1.86–1.97 (m, 1H), 2.45 (qt, 2H), 4.96–5.07 (m, 3H, involving a quartet at 4.97), 6.07 (s, 1H), 8.41 (s, 1H).

Production Example 22

In 4 ml of tetrahydrofuran was suspended 0.13 g of sodium hydride (60% in oil), to which 0.5 ml of a solution containing 0.24 g of 3-methyl-2-butanol was added dropwise at 0° C., followed by stirring for 10 minutes. To this was added dropwise 0.5 ml of a solution containing 0.40 g of 4,6-dichloropyrimidine in tetrahydrofuran, followed by stirring at 0° C. for 3 hours. To this was added dropwise 0.5 ml of a solution containing 0.29 g of 2-pentyn-1-ol in tetrahydrofuran and further added 0.15 g of sodium hydride (60% in oil), followed by stirring at room temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.44 g of 4-(1,2-dimethylpropyloxy)-6-(2-pentynyloxy)pyrimidine (the present compound (22)).

$^1$H-NMR: 0.94 (d, 3H), 0.96 (d, 3H), 1.15 (t, 3H), 1.25 (d, 3H), 1.86–1.97 (m, 1H), 2.45 (qt, 2H), 4.96–5.07 (m, 3H, involving a quartet at 4.97), 6.07 (s, 1H), 8.41 (s, 1H).

Production Example 23

In 4 ml of tetrahydrofuran was suspended 0.10 g of sodium hydride (60% in oil), to which 0.4 ml of a solution containing 0.17 g of 2-butanol was added dropwise at 0° C., followed by stirring for 10 minutes. To this was added dropwise 0.4 ml of a solution containing 0.30 g of 4,6-dichloropyrimidine in tetrahydrofuran, followed by stirring at the same temperature for 3 hours. To this was added dropwise 0.4 ml of a solution containing 0.18 g of 2-butyn-1-ol in tetrahydrofuran and further added 0.10 g of sodium hydride (60% in oil), followed by stirring at room temperature for 7 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.31 g of 4-(sec-butyloxy)-6-(2-butynyloxy)pyrimidine (the present compound (23)).

$^1$H-NMR: 0.94 (t, 3H), 1.30 (d, 3H), 1.59–1.78 (m, 2H), 1.87 (t, 3H), 4.95 (q, 2H), 5.10–5.15 (m, 1H), 6.06 (s, 1H), 8.42 (s, 1H).

Production Example 24

In 2 ml of tetrahydrofuran was suspended 0.05 g of sodium hydride (60% in oil), to which 0.3 ml of a solution containing 0.10 g of 3-methyl-2-butanol was added dropwise at 0° C., followed by stirring for 10 minutes. To this was added dropwise 0.3 ml of a solution containing 0.20 g of 4,5,6-trichloropyrimidine in tetrahydrofuran, followed by stirring at the same temperature for 6 hours. To this was added dropwise 0.3 ml of a solution containing 0.08 g of 2-butyn-1-ol in tetrahydrofuran and further added 0.05 g of sodium hydride (60% in oil), followed by stirring at room temperature for 3 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.15 g of 4-(2-butynyloxy)-5-chloro-6-(1,2-dimethylpropyloxy)pyrimidine (the present compound (24)).

$^1$H-NMR: 0.97–1.00 (m, 6H), 1.30 (d, 3H), 1.87 (t, 3H), 1.93–2.01 (m, 1H), 5.02–5.14 (m, 3H, involving a quartet at 5.03), 8.28 (s, 1H).

Production Example 25

In 2 ml of tetrahydrofuran was suspended 0.06 g of sodium hydride (60% in oil), to which 0.3 ml of a solution containing 0.11 g of 3-methyl-2-butanol was added dropwise at 0° C., followed by stirring for 10 minutes. To this was added dropwise 0.3 ml of a solution containing 0.20 g of 4,6-dichloro-5-methylpyrimidine in tetrahydrofuran, followed by stirring at the same temperature for 5 hours. To this was added dropwise 0.3 ml of a solution containing 0.10 g of 2-butyn-1-ol in tetrahydrofuran and further added 0.06 g of sodium hydride (60% in oil), followed by stirring at room temperature for 3 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.20 g of 4-(2-butynyloxy)-6-(1,2-dimethylpropyloxy)-5-methylpyrimidine (the present compound (25)).

$^1$H-NMR: 0.95–0.98 (m, 6H), 1.26 (d, 3H), 1.86–1.96 (m, 4H, involving a triplet at 1.87), 2.02 (s, 3H), 4.97 (q, 2H), 5.02–5.09 (m, 1H), 8.29 (s, 1H).

Production Example 26

In 4 ml of tetrahydrofuran was suspended 0.10 g of sodium hydride (60% in oil), to which 0.4 ml of a solution containing 0.23 g of 1-cyclopentylethanol was added dropwise at 0° C., followed by stirring for 10 minutes. To this was added dropwise 0.4 ml of a solution containing 0.30 g of 4,6-dichloropyrimidine in tetrahydrofuran, followed by stirring at the same temperature for 4 hours. To this was added dropwise 0.4 ml of a solution containing 0.16 g of 2-butyn-1-ol in tetrahydrofuran and further added 0.10 g of sodium hydride (60% in oil), followed by stirring for 3 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.25 g of 4-(2-butynyloxy)-6-(1-cyclopentylethyloxy)pyrimidine (the present, compound (26)).

$^1$H-NMR: 1.23–1.36 (m, 5H), 1.55–1.87 (m, 8H, involving a triplet at 1.87), 2.02–2.14 (m, 1H), 4.95 (q, 2H), 5.03–5.10 (m, 1H), 6.05 (s, 1H), 8.42 (s, 1H).

Production Example 27

In 4 ml of tetrahydrofuran was suspended 0.10 g of sodium hydride (60% in oil), to which 0.4 ml of a solution containing 0.26 g of 1-cyclohexylethanol was added dropwise at 0° C., followed by stirring for 10 minutes. To this was added dropwise 0.4 ml of a solution containing 0.30 g of 4,6-dichloropyrimidine in tetrahydrofuran, followed by stirring at the same temperature for 4 hours. To this was added dropwise 0.4 ml of a solution containing 0.16 g of 2-butyn-1-ol in tetrahydrofuran and further added 0.10 g of sodium hydride (60% in oil), followed by stirring for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.44 g of 4-(2-butynyloxy)-6-(1-cyclohexylethyloxy)pyrimidine (the present compound (27)).

$^1$H-NMR: 0.88–1.27 (m, 8H, involving a doublet at 1.24), 1.57–1.88 (m, 9H, involving a triplet at 1.87), 4.94 (q, 2H), 4.97–5.06 (m, 1H), 6.05 (s, 1H), 8.41 (s, 1H).

Production Example 28

First, 0.33 g of 4-(2-butynyloxy)-6-(2-hydroxy-2-methylpropyloxy)pyrimidine was dissolved in 3 ml of chloroform, to which 0.5 ml of a solution containing 0.25 g of DAST in chloroform was added dropwise at 0° C., followed by stirring for 30 minutes. The reaction mixture was then poured into water, which was extracted three times with chloroform. The combined organic layers were washed with a saturated aqueous sodium chloride solution, dried over anhydrous magnesium sulfate, and then concentrated. The residue was subjected to silica gel column chromatography to give 0.21 g of 4-(2-butynyloxy)-6-(2-fluoro-2-methylpropyloxy)pyrimidine (the present compound (28)).

$^1$H-NMR: 1.45 (d, 6H), 1.87 (t, 3H), 4.37 (d, 2H), 4.96 (q, 2H), 6.18 (s, 1H), 8.43 (s, 1H).

Production Example 29

First, 0.38 g of 4,6-dichloropyrimidine was dissolved in 5 ml of tetrahydrofuran, to which 0.12 g of sodium hydride (60% in oil) was added and 0.4 ml of a solution containing 0.33 g of 1,1-dichloro-2-propanol in tetrahydrofuran was added dropwise at 0° C., followed by stirring at 0° C. for 2 hours. To this was added dropwise 0.4 ml of a solution containing 0.16 g of 2-butyn-1-ol in tetrahydrofuran at room temperature and further added 0.10 g of sodium hydride (60% in oil), followed by stirring at room temperature for 3 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.32 g of 4-(2-butynyloxy)-6-(2,2-dichloro-1-methylethyloxy)pyrimidine (the present compound (29)).

$^1$H-NMR: 1.55 (d, 3H), 1.87 (t, 3H), 4.95 (q, 2H), 5.54–5.62 (m, 1H), 6.05 (m, 1H), 6.16 (s, 1H), 8.43 (s, 1H).

Production Example 30

In 4 ml of tetrahydrofuran was suspended 0.11 g of sodium hydride (60% in oil), to which 0.4 ml of a solution containing 0.23 g of 2,4-dimethyl-3-pentanol was added dropwise at 0° C., followed by stirring for 10 minutes. To this was added dropwise 0.4 ml of a solution containing 0.30 g of 4,6-dichloropyrimidine in tetrahydrofuran, followed by stirring at the same temperature for 3 hours. To this was added dropwise 0.4 ml of a solution containing 0.17 g of 2-butyn-1-ol in tetrahydrofuran at room temperature and further added 0.11 g of sodium hydride (60% in oil), followed by stirring for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.44 g of 4-(2-butynyloxy)-6-(1-isopropyl-2-methylpropyloxy)pyrimidine (the present compound (30)).

$^1$H-NMR: 0.91 (d, 12H), 1.88 (t, 3H), 1.96–2.04 (m, 2H), 4.95 (q, 2H), 5.05–5.08 (m, 1H), 6.07 (s, 1H), 8.39 (s, 1H).

Production Example 31

In 2 ml of tetrahydrofuran was suspended 0.03 g of sodium hydride (60% in oil), to which 0.3 ml of a solution containing 0.26 g of 4-chloro-6-(2-hydroxy-1,2-dimethylpropyloxy)pyrimidine was added dropwise at room temperature, followed by stirring for 10 minutes. To this was added dropwise 0.3 ml of a solution containing 0.11 g of iodomethane in tetrahydrofuran, followed by further stirring at the same temperature for 4 hours. To this was added dropwise 0.3 ml of a solution containing 0.06 g of 2-butyn-1-ol in tetrahydrofuran at room temperature and further added 0.03 g of sodium hydride (60% in oil), followed by stirring for 5 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.04 g of 4-(2-butynyloxy)-6-(2-methoxy-1,2-dimethylpropyloxy)pyrimidine (the present compound (31)).

$^1$H-NMR: 1.21 (s, 3H), 1.22 (s, 3H), 1.28 (d, 3H), 1.87 (t, 3H), 3.26 (s, 3H), 4.94 (q, 2H), 5.28 (q, 1H), 6.10 (s, 1H), 8.42 (s, 1H).

Production Example 32

In 1.5 ml of tetrahydrofuran was suspended 0.04 g of sodium hydride (60% in oil), to which 0.3 ml of a solution containing 0.07 g of 2-butyn-1-ol was added dropwise at room temperature, followed by stirring for 10 minutes. To this was added dropwise 0.3 ml of a solution containing 0.23 g of 4-chloro-6-(2,2-dichloro-1-methylcyclopropylmethyloxy)pyrimidine in tetrahydrofuran at 0° C., followed by stirring at room temperature for 7 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.22 g of 4-(2-butynyloxy)-6-(2,2-dichloro-1-methylcyclopropyl)methoxypyrimidine (the present compound (32)).

$^1$H-NMR: 1.36 (d, 1H), 1.50 (s, 3H), 1.56 (d, 1H), 1.88 (t, 3H), 4.34 (d, 1H), 4.58 (d, 1H), 4.96 (q, 2H), 6.18 (s, 1H), 8.43 (s, 1H).

Production Example 33

In 7 ml of tetrahydrofuran was suspended 0.24 g of sodium hydride (60% in oil), to which 1 ml of a solution containing 0.28 g of propargyl alcohol was added dropwise at room temperature, followed by stirring for 10 minutes. To this was added dropwise 1 ml of a solution containing 1 g of 4-chloro-6-(1,2-dimethylpropyloxy)pyrimidine in tetrahydrofuran at the same temperature, followed by stirring at room temperature for 5 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 1.24 g of 4-(1,2-dimethylpropyloxy)-6-(2-propynloxy)pyrimidine (the present compound (33)).

$^1$H-NMR: 0.95 (d, 3H), 0.98 (d, 3H), 1.26 (d, 3H), 1.88–1.96 (m, 1H), 2.50 (t, 1H), 4.98–5.05 (m, 3H), 6.07 (s, 1H), 8.44 (s, 1H).

Production Example 34

In 3 ml of carbon tetrachloride were dissolved 0.23 g of 4-(2-butynyloxy)-6-(1,2-dimethylallyloxy)pyrimidine and 0.01 g of trioctylmethylammonium chloride, to which 1 ml of concentrated hydrochloric acid was added dropwise at 0° C., followed by stirring at 0° C. for 30 minutes and at room temperature for 3 hours. The reaction mixture was then poured into water, which was extracted three times with t-butyl methyl ether. The combined organic layer was washed with a saturated aqueous sodium hydrogencarbonate solution, a saturated aqueous sodium chloride solution, dried over anhydrous magnesium, and then concentrated. The residue was subjected to silica gel column chromatography to give 0.05 g of 4-(2-butynyloxy)-6-(2-chloro-1,2-dimethylpropyloxy)pyrimidine (the present compound (34)).

$^1$H-NMR: 1.41 (d, 3H), 1.60 (s, 6H), 1.87 (t, 3H), 4.95 (q, 2H), 5.41 (q, 1H), 6.12 (s, 1H), 8.43 (s, 1H).

Production Example 35

In 4 ml of tetrahydrofuran was suspended 0.11 g of sodium hydride (60% in oil), to which 0.4 ml of a solution containing 0.30 g of 2,2,2-trichloro ethanol was added dropwise at 0° C., followed by stirring for 10 minutes. To this was added dropwise 0.4 ml of a solution containing 0.30 g of 4,6-dichloropyrimidine in tetrahydrofuran, followed by stirring at the same temperature for 2 hours. To this was added dropwise 0.4 ml of a solution containing 0.17 g of 2-butyn-1-ol at room temperature and further added 0.11 g of sodium hydride (60% in oil), followed by stirring for 3 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.20 g of 4-(2-butynyloxy)-6-(2,2,2-trichloroethyloxy)pyrimidine (the present compound (35)).

$^1$H-NMR: 1.88 (t, 3H), 4.98 (q, 2H), 5.08 (s, 2H), 6.29 (s, 1H), 8.46 (s, 1H).

Production Example 36

In 6 ml of tetrahydrofuran was suspended 0.15 g of sodium hydride (60% in oil), to which 0.4 ml of a solution containing 0.45 g of 3,3-dichloro-2-butanol was added dropwise at 0° C., followed by stirring for 10 minutes. To this was added dropwise 0.4 ml of a solution containing 0.47 g of 4,6-dichloropyrimidine in tetrahydrofuran, followed by stirring at the same temperature for 4 hours. To this was added dropwise 0.4 ml of a solution containing 0.17 g of 2-butyn-1-ol at room temperature and further added 0.19 g of sodium hydride (60% in oil), followed by stirring for 2 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.39 g of 4-(2-butynyloxy)-6-(2,2-dichloro-1-methylpropyloxy)pyrimidine (the present compound (36)).

$^1$H-NMR: 1.57 (d, 3H), 1.88 (t, 3H), 2.16 (s, 3H), 4.96 (q, 2H), 5.72 (q, 12H), 6.17 (s, 1H), 8.45 (s, 1H).

Production Example 37

In 1.5 ml of tetrahydrofuran was suspended 0.04 g of sodium hydride (60% in oil), to which 0.5 ml of a solution containing 0.07 g of 2-butyn-1-ol was added dropwise at room temperature, followed by stirring for 10 minutes. To this was added dropwise 0.5 ml of a solution containing 0.18 g of 4-chloro-6-(2,2-dichloropropyloxy)pyrimidine in tetrahydrofuran, followed by stirring for 2 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.08 g of 4-(2-butynyloxy)-6-(2,2-dichloropropyloxy)pyrimidine (the present compound (37)).

$^1$H-NMR: 1.87 (t, 3H), 2.19 (s, 3H), 4.78 (s, 2H), 4.98 (q, 2H), 6.22 (s, 1H), 8.45 (s, 1H).

Production Example 38

In 3 ml of tetrahydrofuran was suspended 0.10 g of sodium hydride (60% in oil), to which 0.4 ml of a solution containing 0.33 g of 3,3,3-trichloro-2-propanol was added dropwise at room temperature, followed by stirring for 10 minutes. To this was added dropwise 0.4 ml of a solution containing 0.3 g of 4,6-dichloropyrimidine in tetrahydrofuran at 0° C., followed by stirring at the same temperature for 30 minutes. To this was added dropwise 0.4 ml of a solution containing 0.20 g of 2-pentyn-1-ol at room temperature and further added 0.10 g of sodium hydride (60% in oil), followed by stirring for 2 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.47 g of 4-(2-pentynyloxy)-6-(2,2,2-trichloro-1-methylethoxy)pyrimidine (the present compound (38)).

$^1$H-NMR: 1.15 (t, 3H), 1.67 (d, 3H), 2.25 (qt, 2H), 4.99 (t, 2H), 6.02 (q, 1H), 6.22 (s, 1H), 8.45 (s, 1H).

Production Example 39

In 3 ml of tetrahydrofuran was suspended 0.09 g of sodium hydride (60% in oil), to which 0.4 ml of a solution containing 0.31 g of 1,1-dichloro-3,3-dimethyl-2-butanol was added dropwise at room temperature, followed by stirring for 10 minutes. To this was added dropwise 0.4 ml of a solution containing 0.27 g of 4,6-dichloropyrimidine in tetrahydrofuran at 0° C., followed by stirring at the same temperature for 2.5 hours. To this was added dropwise 0.4 ml of a solution containing 0.15 g of 2-butyn-1-ol in tetrahydrofuran at room temperature and further added 0.09 g of sodium hydride (60% in oil), followed by stirring for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.45 g of 4-(2-butynyloxy)-6-(1-(dichloromethyl)-2,2-dimethylpropyloxy)pyrimidine (the present compound (39)).

$^1$H-NMR: 1.08 (s, 9H), 1.88 (t, 3H), 4.97 (q, 2H), 5.79 (d, 1H), 6.06 (d, 1H), 6.24 (s, 1H), 8.44 (s, 1H).

Production Example 40

In 5 ml of chloroform were dissolved 0.64 g of 4-(2-pentynyloxy)-6-(2-methyl-2-propenyloxy)pyrimidine and 0.06 g of trioctylmethylammonium chloride, to which 3 ml of concentrated hydrochloric acid was added dropwise at 0° C., followed by stirring at 0° C. for 30 minutes and at room temperature for 7 hours. The reaction mixture was then poured into water, which was extracted three times with t-butyl methyl ether. The combined organic layer was washed with a saturated aqueous sodium hydrogencarbonate solution, a saturated aqueous sodium chloride solution, dried over anhydrous magnesium, and then concentrated. The residue was subjected to silica gel column chromatography to give 0.12 g of 4-(2-pentynyloxy)-6-(2-chloro-2-methylpropyloxy)pyrimidine (the present compound (40)).

$^1$H-NMR: 1.15 (t, 3H), 1.66 (s, 6H), 2.24 (qt, 2H), 4.42 (s, 2H), 4.97 (t, 2H), 6.18 (s, 1H), 8.43 (s, 1H).

Production Example 41

To a solution containing 0.3 g of 4-(2-pentynyloxy)-6-(1,2-dimethyl-2-propenyloxy)pyrimidine in 3 ml of tetrahydrofuran was added dropwise 3.66 ml of a 1 mol/l solution of hydrogen chloride in diethyl ether, followed by stirring at room temperature for 9 hours. The reaction mixture was then poured into a saturated aqueous sodium hydrogencarbonate solution, which was extracted three times with t-butyl methyl ether. The combined organic layers were washed with a saturated aqueous sodium chloride solution, dried over anhydrous magnesium chloride, and then concentrated. The residue was subjected to silica gel column chromatography to give 0.07 g of 4-(2-pentynyloxy)-6-(2-chloro-1,2-dimethylpropyloxy)pyrimidine (the present compound (41)).

$^1$H-NMR: 1.15 (t, 3H), 1.31 (d, 3H), 1.64 (s, 6H), 2.25 (qt, 2H), 4.96 (t, 2H), 5.39 (q, 1H), 6.13 (s, 1H), 8.42 (s, 1H).

The present compounds described in the above production examples are listed together with their compound numbers in Tables 1 and 2.

The compounds of formula (1):

TABLE 1

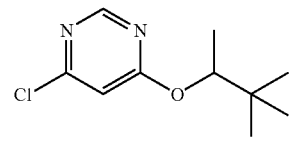

(1)

| Compound No. | R¹ | R² | R³ |
|---|---|---|---|
| 1 | CH₂C≡CCH₃ | H | CH(CH₃)₂ |
| 2 | CH₂C≡CCH₃ | H | CH(CH₃)-cC₃H₅ |
| 3 | CH₂C≡CCH₃ | H | CH(CH₃)C(CH₃)₃ |
| 4 | CH₂C≡CCH₃ | H | CH(C₂H₅)C(CH₃)₃ |
| 5 | CH₂C≡CCH₃ | H | CH(CH₃)CH₂CH(CH₃)₂ |
| 6 | CH₂C≡CCH₃ | H | CHC(CH₃)₃ |
| 7 | CH₂C≡CCH₃ | H | CH(CH₃)CH₂C(CH₃)₃ |
| 8 | CH₂C≡CCH₃ | H | CH(CH₃)-X¹ |
| 9 | CH₂C≡CCH₃ | H | CH₂C(CF₃)₂CH₃ |
| 10 | CH₂C≡CCH₃ | H | CH₂CH(CH₃)₂CH₂Cl |
| 11 | CH₂C≡CCH₃ | H | CH₂CH₂C(CH₃)₃ |
| 12 | CH₂C≡CCH₃ | H | CH(CH₃)CH(CH₃)₂ |
| 13 | CH₂C≡CCH₃ | H | CH₂C(CH₃)₂CH₂Br |
| 14 | CH₂C≡CCH₃ | H | CH(CH₃)CF(CH₃)₂ |
| 15 | CH₂C≡CCH₃ | H | CH₂CH(CH₃)₂ |
| 16 | CH₂C≡CCH₃ | H | CH(CH₃)CH(CH₃)C₂H₅ |
| 17 | CH₂C≡CC₂H₅ | H | CH(CH₃)CF(CH₃)₂ |
| 18 | CH₂C≡CCH₃ | H | CH(CH₃)CH(OCH₃)₂ |
| 19 | CH₂C≡CCH₃ | H | CH(CH₃)CCl₃ |
| 20 | CH₂C≡CCH₃ | H | CH₂CCl(CH₃)₂ |
| 21 | CH₂C≡CCH₃ | H | CH(CH₃)cC₄H₇ |
| 22 | CH₂C≡CC₂H₅ | H | CH(CH₃)CH(CH₃)₂ |
| 23 | CH₂C≡CCH₃ | H | CH(CH₃)C₂H₅ |
| 24 | CH₂C≡CCH₃ | Cl | CH(CH₃)CH(CH₃)₂ |
| 25 | CH₂C≡CCH₃ | CH₃ | CH(CH₃)CH(CH₃)₂ |

TABLE 2

| Compound No. | R¹ | R² | R³ |
|---|---|---|---|
| 26 | CH₂C≡CCH₃ | H | CH(CH₃)cC₅H₉ |
| 27 | CH₂C≡CCH₃ | H | CH(CH₃)cC₆H₁₁ |
| 28 | CH₂C≡CCH₃ | H | CH₂CF(CH₃)₂ |
| 29 | CH₂C≡CCH₃ | H | CH(CH₃)CHCl₂ |
| 30 | CH₂C≡CCH₃ | H | CH[CH(CH₃)₂]₂ |
| 31 | CH₂C≡CCH₃ | H | CH(CH₃)C(CH₃)₂OCH₃ |
| 32 | CH₂C≡CCH₃ | H | CH₂-X² |
| 33 | CH₂C≡CH | H | CH(CH₃)CH(CH₃)₂ |
| 34 | CH₂C≡CCH₃ | H | CH(CH₃)CCl(CH₃)₂ |
| 35 | CH₂C≡CCH₃ | H | CH₂CCl₃ |
| 36 | CH₂C≡CCH₃ | H | CH(CH₃)CCl₂CH₃ |
| 37 | CH₂C≡CCH₃ | H | CH₂CCl₂CH₃ |
| 38 | CH₂C≡CC₂H₅ | H | CH(CH₃)CCl₃ |
| 39 | CH₂C≡CCH₃ | H | CH(C(CH₃)₃)CHCl₂ |
| 40 | CH₂C≡CC₂H₅ | H | CH₂CCl(CH₃)₂ |
| 41 | CH₂C≡CC₂H₅ | H | CH(CH₃)CCl(CH₃)₂ |

In the tables, "c" means cyclo-, and X¹ and X² mean, respectively, the followings groups:

X¹ = 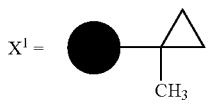    X² = 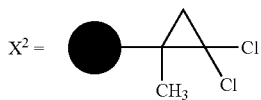

The following will reference production examples for the production of intermediates in the production of the present compounds.

Reference Production Example 1

In 3.5 ml of tetrahydrofuran was suspended 0.11 g of sodium hydride (60% in oil), to which 0.5 ml of tetrahydrofuran containing 0.12 g of isopropyl alcohol dissolved therein was added dropwise at 0° C., followed by stirring for 10 minutes. To this was added dropwise 0.5 ml of tetrahydrofuran containing 0.3 g of 4,6-dichloropyrimidine dissolved therein, followed by stirring at 0° C. for 2 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.26 g of 4-chloro-6-isopropyloxypyrimidine.

¹H-NMR: 1.36 (d, 6H), 5.33–5.43 (m, 1H), 6.70 (s, 1H), 8.55 (s, 1H).

Reference Production Example 2

In 4 ml of tetrahydrofuran was suspended 0.11 g of sodium hydride (60% in oil), to which 0.5 ml of tetrahydrofuran containing 0.23 g of 3,3-dimethyl-2-butanol dissolved therein was added dropwise at room temperature, followed by stirring for 10 minutes. To this was added dropwise 0.5 ml of tetrahydrofuran containing 0.3 g of 4,6-dichloropyrimidine dissolved therein, followed by stirring at the same temperature for 6 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.24 g of 4-chloro-6-(1,2,2-trimethylpropyloxy)pyrimidine.

4-Chloro-6-(1,2,2-trimethylpropyloxy)pyrimidine

¹H-NMR: 0.96 (s, 9H), 1.24 (d, 3H), 5.08 (q, 1H), 6.73 (s, 1H), 8.54 (s, 1H).

Reference Production Example 3

In 4 ml of tetrahydrofuran was suspended 0.11 g of sodium hydride (60% in oil), to which 0.5 ml of tetrahydrofuran containing 0.26 g of 2,2-dimethyl-3-pentanol dissolved therein was added dropwise at room temperature, followed by stirring for 10 minutes. To this was added dropwise 0.5 ml of tetrahydrofuran containing 0.3 g of 4,6-dichloropyrimidine dissolved therein at 0° C., followed by stirring at the same temperature for 1 hour and at room temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.35 g of 4-chloro-6-(1-ethyl-2,2-dimethylpropyloxy)pyrimidine.

4-Chloro-6-(1-ethyl-2,2-dimethylpropyloxy)pyrimidine

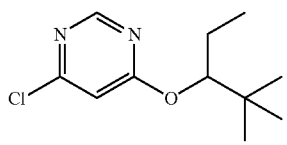

$^1$H-NMR: 0.86 (t, 3H), 0.93 (s, 9H), 1.58–1.78 (m, 2H), 5.25 (dd, 1H), 6.75 (s, 1H), 8.52 (s, 1H).

Reference Production Example 4

In 4 ml of tetrahydrofuran was suspended 0.10 g of sodium hydride (60% in oil), to which 0.5 ml of tetrahydrofuran containing 0.14 g of 2,2-dimethyl-1-propanol dissolved therein was added dropwise at room temperature, followed by stirring for 10 minutes. To this was added dropwise 0.5 ml of tetrahydrofuran containing 0.3 g of 4,6-dichloropyrimidine dissolved therein at 0° C., followed by stirring at the same temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.16 g of 4-chloro-6-(2,2-dimethylpropyloxy)pyrimidine.

4-Chloro-6-(2,2-dimethylpropyloxy)pyrimidine

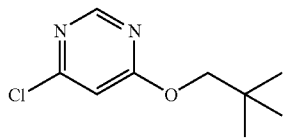

$^1$H-NMR: 0.86 (t, 3H), 0.93 (s, 9H), 1.58–1.78 (m, 2H), 5.25 (dd, 1H), 6.75 (s, 1H), 8.52 (s, 1H).

Reference Production Example 5

In 4 ml of tetrahydrofuran was suspended 0.13 g of sodium hydride (60% in oil), to which 5.4 ml of a 0.5 mol/l solution containing 1-(1-methylcyloropropyl)ethanol was added dropwise at 0° C., followed by stirring for 10 minutes. To this was added dropwise 0.5 ml of tetrahydrofuran containing 0.4 g of 4,6-dichloropyrimidine dissolved therein at 0° C., followed by stirring at the same temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.18 g of 4-chloro-6-[1-(1-methylcyclopropyl)ethyloxy]pyrimidine.

4-Chloro-6-[1-(1-methylcyclopropyl)ethyloxy]pyrimidine

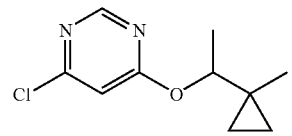

$^1$H-NMR: 0.29–0.38 (m, 2H), 0.42–0.45 (m, 1H), 0.53–0.64 (m, 1H), 1.12 (s, 3H), 1.34 (d, 3H), 4.75 (q, 1H), 6.72 (s, 1H), 8.49 (s, 1H).

Reference Production Example 6

In 5 ml of tetrahydrofuran was suspended 0.14 g of sodium hydride (60% in oil), to which 0.5 ml of a solution containing 0.36 g of 3-chloro-2,2-dimethyl-1-propanol was added dropwise at 0° C., followed by stirring for 10 minutes. To this was added dropwise 0.5 ml of tetrahydrofuran containing 0.4 g of 4,6-dichloropyrimidine dissolved therein, followed by stirring at the same temperature for 2 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.62 g of 4-chloro-6-(3-chloro-2,2-dimethylpropyloxy)pyrimidine.

4-Chloro-6-(3-chloro-2,2-dimethylpropyloxy)pyrimidine

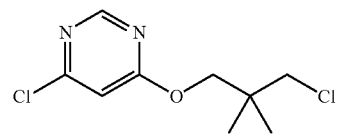

$^1$H-NMR: 1.11 (s, 6H), 3.51 (s, 2H), 4.23 (s, 2H), 6.81 (s, 1H), 8.57 (s, 1H).

Reference Production Example 7

In 4 ml of tetrahydrofuran was suspended 0.11 g of sodium hydride (60% in oil), to which 0.5 ml of a solution containing 0.23 g of 3,3-dimethyl-1-butanol was added dropwise at 0° C., followed by stirring for 10 minutes. To this was added dropwise 0.5 ml of tetrahydrofuran containing 0.3 g of 4,6-dichloropyrimidine dissolved therein, followed by stirring at the same temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.41 g of 4-chloro-6-(3,3-dimethylbutyloxy)pyrimidine.

4-Chloro-6-(3,3-dimethylbutyloxy)pyrimidine

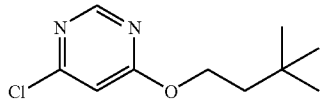

¹H-NMR: 0.99 (s, 9H), 1.70 (t, 2H), 4.44 (t, 2H), 6.73 (s, 1H), 8.57 (s, 1H).

Reference Production Example 8

In 4 ml of tetrahydrofuran was suspended 0.10 g of sodium hydride (60% in oil), to which 0.5 ml of a solution containing 0.18 g of 3-methyl-2-butanol was added dropwise at 0° C., followed by stirring for 10 minutes. To this was added dropwise 0.5 ml of tetrahydrofuran containing 0.3 g of 4,6-dichloropyrimidine dissolved therein, followed by stirring at the same temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.35 g of 4-chloro-6-(1,2-dimethylpropyloxy)pyrimidine.

4- Chloro-6-(1,2-dimethylpropyloxy)pyrimidine

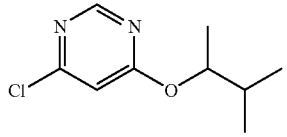

¹H-NMR: 0.95 (d, 3H), 0.97 (d, 3H), 1.27 (d, 3H), 1.78–2.14 (m, 1H), 5.10–5.16 (m, 1H), 6.73 (s, 1H), 8.54 (s, 1H).

Reference Production Example 9

In 4 ml of tetrahydrofuran was suspended 0.10 g of sodium hydride (60% in oil), to which 0.5 ml of a solution containing 0.34 g of 3-bromo-2,2-dimethyl-1-propanol was added dropwise at 0° C., followed by stirring for 10 minutes. To this was added dropwise 0.5 ml of tetrahydrofuran containing 0.3 g of 4,6-dichloropyrimidine dissolved therein, followed by stirring at the same temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.56 g of 4-chloro-6-(3-bromo-2,2-dimethylpropyloxy)pyrimidine.

4-Chloro-6-(3-bromo-2,2-dimethylpropyloxy)pyrimidine

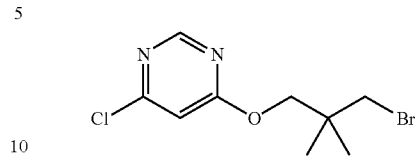

¹H-NMR: 1.11 (s, 6H), 3.51 (s, 2H), 4.23 (s, 2H), 6.81 (s, 1H), 8.57 (s, 1H).

Reference Production Example 10

In 8 ml of tetrahydrofuran was suspended 0.41 g of sodium hydride (60% in oil), to which 0.6 ml of a solution containing 0.49 g of 2-methylbutane-2,3-diol was added dropwise at 0° C., followed by stirring for 10 minutes. To this was added dropwise 0.6 ml of tetrahydrofuran containing 0.69 g of 4,6-dichloropyrimidine dissolved therein, followed by stirring at the same temperature for 4.5 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.74 g of 4-chloro-6-(2-hydroxy-1,2-dimethylpropyloxy)pyrimidine.

4-Chloro-6-(2-hydroxy-1,2-dimethylpropyloxy)pyrimidine

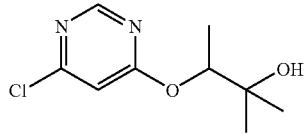

¹H-NMR: 1.27 (s, 3H), 1.28 (s, 3H), 1.33 (d, 3H), 1.97 (s, 1H), 5.22 (q, 1H), 6.79 (s, 1H), 8.56 (s, 1H).

Reference Production Example 11

In 3 ml of tetrahydrofuran was suspended 0.17 g of sodium hydride (60% in oil), to which 0.4 ml of a solution containing 0.17 g of 2-pentyn-1-ol was added dropwise at 0° C., followed by stirring for 10 minutes. To this was added dropwise 0.4 ml of tetrahydrofuran containing 0.37 g of 3-(6-chloro-4-pyrimidyloxy)-2-methyl-2-butanol dissolved therein, followed by stirring at the same temperature for 1 hour and at room temperature for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.33 g of 4-(2-pentynyloxy)-6-(2-hydroxy-1,2-dimethylpropyloxy)pyrimidine.

4-(2-Pentynyloxy)-6-(2-hydroxy-1,2-dimethylpropyloxy)pyrimidine

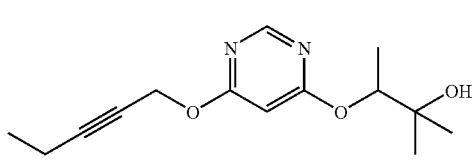

$^1$H-NMR: 1.15 (t, 3H), 1.17 (s, 3H), 1.27 (s, 3H), 1.31 (d, 3H), 2.24 (qt, 2H), 4.97 (t, 2H), 5.11 (q, 1H), 6.12 (s, 1H), 8.42 (s, 1H).

Reference Production Example 12

In 5 ml of tetrahydrofuran was suspended 0.13 g of sodium hydride (60% in oil), to which 5.4 ml of a 0.5 mol/l solution containing 1,1-dimethoxy-2-propanol in tetrahydrofuran was added dropwise at 0° C., followed by stirring for 10 minutes. To this was added dropwise 0.5 ml of tetrahydrofuran containing 0.4 g of 4,6-dichloropyrimidine dissolved therein, followed by stirring at 0° C. for 4 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.16 g of 4-chloro-6-(2,2-dimethoxy-1-methylethoxy)pyrimidine.

4-Chloro-6-(2,2-dimethoxy-1-methylethoxy)pyrimidine

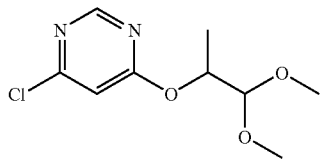

$^1$H-NMR: 1.34 (d, 3H), 3.42 (s, 3H), 3.45 (s, 3H), 4.40 (d, 1H), 5.42 (dt, 1H), 6.78 (s, 1H), 8.56 (s, 1H).

Reference Production Example 13

In 4 ml of tetrahydrofuran was suspended 0.11 g of sodium hydride (60% in oil), to which 0.5 ml of a solution containing 0.16 g of 2-methyl-2-propenol in tetrahydrofuran was added dropwise at 0° C., followed by stirring for 10 minutes. To this was added dropwise 0.5 ml of a solution containing 0.4 g of 4-(2-butynyloxy)-6-chloropyrimidine in tetrahydrofuran, followed by stirring at the same temperature for 2 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.15 g of 4-(2-butynyloxy)-6-(2-methylallyloxy)pyrimidine.

4-(2-Butynyloxy)-6-(2-methylallyloxy)pyrimidine

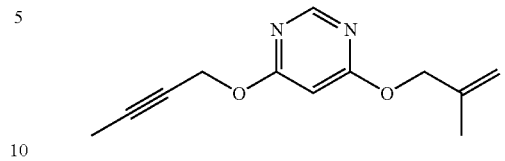

$^1$H-NMR: 1.81 (s, 3H), 1.87 (t, 3H), 4.77 (s, 2H), 4.94–4.97 (m, 3H), 5.04 (s, 1H), 6.14 (s, 1H), 8.44 (s, 1H).

Reference Production Example 14

In 20 ml of tetrahydrofuran was dissolved 1 g of 1-hydroxy-2-propanone, to which 26 ml of a 1.14 mol/l solution (diethyl ether solution) of methyl lithium was added dropwise at −78° C. The mixture was stirred at the same temperature for 1 hour. After gradually increasing the temperature up to 0° C., 4 ml of a solution containing 2 g of 4,6-dichloropyrimidine in tetrahydrofuran was added dropwise, followed by further stirring 2 hours. The reaction mixture was then poured into a saturated aqueous ammonium chloride solution, which was extracted three times with ethyl acetate. The combined organic layers were washed with a saturated aqueous sodium chloride solution, dried over anhydrous magnesium sulfate, and then concentrated. The residue was subjected to silica gel column chromatography to give 0.66 g of 4-chloro-6-(2-hydroxy-2-methylpropyloxy)pyrimidine.

4-Chloro-6-(2-hydroxy-2-methylpropyloxy)pyrimidine

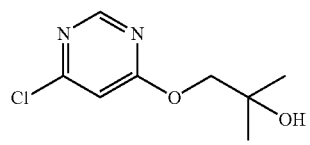

$^1$H-NMR: 1.32 (s, 6H), 2.26 (bs, 1H), 4.28 (s, 2H), 6.85 (s, 1H), 8.57 (s, 1H).

Reference Production Example 15

In 6 ml of tetrahydrofuran was suspended 0.29 g of sodium hydride (60% in oil), to which 0.4 ml of a solution containing 0.25 g of 2-butyn-1-ol in tetrahydrofuran was added dropwise at room temperature, followed by stirring for 10 minutes. To this was added dropwise 0.4 ml of a solution containing 0.66 g of 1-(6-chloropyrimidin-4-yloxy)-2-methyl-2-propanol in tetrahydrofuran at 0° C., followed by increasing the temperature up to room temperature and stirring for 5 hours. The reaction mixture was then poured into a saturated aqueous ammonium chloride solution, which was extracted three times with ethyl acetate. The combined organic layers were washed with a saturated aqueous sodium chloride solution, dried over anhydrous magnesium sulfate, and then concentrated. The residue was subjected to silica gel column chromatography to give 0.33 g of 4-(2-butynyloxy)-6-(2-hydroxy-2-methylpropyloxy)pyrimidine.

4-(2-Butynyloxy)-6-(2-hydroxy-2-methylpropyloxy)pyrimidine

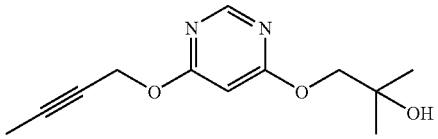

$^1$H-NMR: 1.31 (s, 6H), 1.87 (t, 3H), 3.02 (bs, 1H), 4.22 (s, 2H), 4.96 (q, 2H), 6.16 (s, 1H), 8.43 (s, 1H).

Reference Production Example 16

In 5 ml of tetrahydrofuran was suspended 0.24 g of sodium hydride (60% in oil), to which 0.4 ml of a solution containing 0.26 g of 2-methylbutan-2,3-diol in tetrahydrofuran was added dropwise at 0° C., followed by stirring for 10 minutes. To this was added dropwise 0.4 ml of a solution containing 0.38 g of 4,6-dichloropyrimidin in tetrahydrofuran, followed by stirring at 0° C. for 4 hours. To this was added dropwise 0.4 ml of a solution containing 0.20 g of 2-butyn-1-ol and further added 0.12 g of sodium hydride (60% in oil), followed by stirring at room temperature for 3.5 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.41 g of 4-(2-butynyloxy)-6-(2-hydroxy-1,2-dimethylpropyloxy)pyrimidine.

4-(2-Butynyloxy)-6-(2-hydroxy-1,2-dimethylpropyloxy)pyrimidine

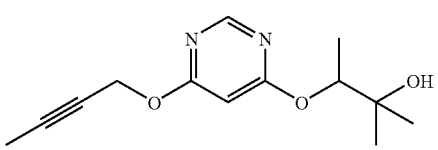

$^1$H-NMR: 1.26 (s, 6H), 1.30 (d, 3H), 1.87 (t, 3H), 2.45 (bs, 1H), 4.95 (q, 2H), 5.11 (q, 1H), 6.11 (s, 1H), 8.42 (s, 1H).

Reference Production Example 17

In 10 ml of tetrahydrofuran was suspended 0.322 g of sodium hydride (60% in oil), to which 0.5 ml of a solution containing 0.16 g of 2-methyl-2-propenol in tetrahydrofuran was added dropwise at 0° C., followed by stirring for 10 minutes. To this was added dropwise 0.5 ml of a solution containing 1 g of 4,6-dichloropyrimidine in tetrahydrofuran, followed by stirring at the same temperature for 2 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 1.27 g of 4-chloro-6-(2-methylallyloxy)pyrimidine.

4-Chloro-6-(2-methylallyloxy)pyrimidine

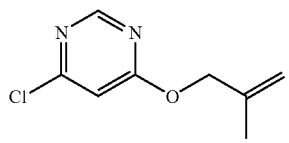

$^1$H-NMR: 1.82 (s, 3H), 4.82 (s, 2H), 4.99 (s, 1H), 5.05 (s, 1H), 6.81 (s, 1H), 8.57 (s, 1H).

Reference Production Example 18

In 6.5 ml of chloroform was dissolved 0.6 g of 4-chloro-6-(2-methylallyloxy)pyrimidine, to which 0.02 g of benzyltriethylammonium chloride was added at 0° C. and 3.25 ml of a 50% sodium hydroxide solution was further added dropwise at the same temperature, followed by stirring at room temperature for 14 hours. The reaction mixture was then poured into water, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.23 g of 4-chloro-6-[(2,2-dichloro-1-methylcyclopropyl)methoxy]pyrimidine.

4-Chloro-6-[(2,2-dichloro-1-methylcyclopropyl)methoxy]pyrimidine

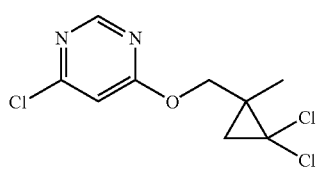

$^1$H-NMR: 1.39 (d, 1H), 1.51 (s, 3H), 1.57 (d, 1H), 4.38 (d, 1H), 4.65 (d, 1H), 6.88 (s, 1H), 8.57 (s, 1H).

Reference Production Example 19

In 3 ml of chloroform was dissolved 0.42 g of 3-[6-(2-butynyloxy)pyrimidin-4-yloxy]-2-methyl-2-butanol, to which 0.2 g of pyridine was added and 0.15 ml of thionyl chloride was added dropwise at −13° C., followed by stirring 2 hours. The reaction mixture was then poured into water, which was extracted three times with chloroform. The combined organic layers were washed with a saturated aqueous sodium hydrogencarbonate, a saturated aqueous sodium chloride solution, dried over anhydrous magnesium sulfate, and then concentrated. The residue was subjected to silica gel column chromatography to give 0.23 g of 4-(2-butynyloxy)-6-(1,2-dimethylallyloxy)pyrimidine.

4-(2-Butynyloxy)-6-(1,2-dimethylallyloxy)pyrimidine

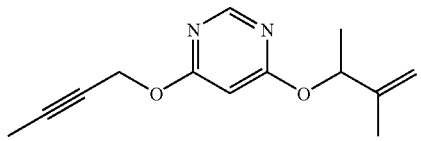

¹H-NMR: 1.42 (d, 3H), 1.78 (s, 3H), 1.87 (t, 3H), 4.86 (s, 1H), 4.95 (q, 2H), 5.01 (s, 1H), 5.55 (q, 1H), 6.12 (s, 1H), 8.42 (s, 1H).

Reference Production Example 20

First, 0.23 g of 4,6-dichloropyrimidine and 0.2 g of 2,2-dichloro-1-propanol were dissolved in 2 ml of tetrahydrofuran, to which 0.07 g of sodium hydride (60% in oil) was added at 0° C., followed by stirring at the same temperature for 2 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel chromatography to give 0.18 g of 4-chloro-6-(2,2-dichloropropyloxy)pyrimidine.

4-Chloro-6-(2,2-dichloropropyloxy)pyrimidine

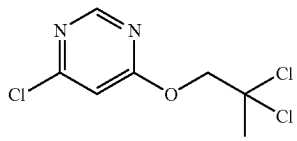

¹H-NMR: 2.21 (s, 3H), 4.80 (s, 2H), 6.93 (s, 1H), 8.60 (s, 1H).

Reference Production Example 21

In 10 ml of tetrahydrofuran was suspended 0.19 g of sodium hydride (60% in oil), to which 0.5 ml of a solution containing 0.57 g of 2-pentyn-1-ol in tetrahydrofuran was added dropwise at room temperature, followed by stirring for 10 minutes. To this was added dropwise 0.4 ml of a solution con-taining 0.3 g of 4,6-dichloropyrimidin in tetrahydrofuran at 0° C., followed by stirring for 1 hour. To this was added dropwise 0.5 ml of a solution containing 0.48 g of 2-methyl-2-propen-1-ol in tetrahydrofuran at the same temperature and further added 0.19 g of sodium hydride (60% in oil), followed by stirring at 2 hours. The reaction mixture was then poured into a saturated aqueous ammonium chloride solution, which was extracted three times with t-butyl methyl ether. The combined organic layers were washed with a saturated aqueous sodium chloride solution, dried over anhydrous magnesium sulfate, and then concentrated. The residue was subjected to silica gel column chromatography to give 0.64 g of 4-(2-methyl-2-propenyloxy)-6-(2-pentynyloxy)pyrimidine.

4-(2-Methyl-2-propenyloxy)-6-(2-pentynyloxy)pyrimidine

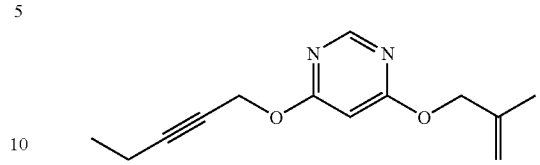

¹H-NMR: 1.15 (t, 3H), 1.81 (s, 3H), 2.25 (qt, 2H), 4.77 (s, 2H), 4.96–4.98 (m, 3H), 5.04 (s, 1H), 6.15 (s, 1H), 8.44 (s, 1H).

Reference Production Example 22

In 3 ml of chloroform was dissolved 0.5 g of 4-(2-pentynyloxy)-6-(2-hydroxy-1,2-dimethylpropyloxy)pyrimidine, to which 0.18 g of pyridine was added and 0.27 g of thionyl chloride was added dropwise at −13° C., followed by stirring for 1.5 hours. The reaction mixture was then poured into water, which was extracted three times with chloroform. The combined organic layers were washed with a saturated aqueous sodium hydrogencarbonate solution, a saturated aqueous sodium chloride solution, dried over anhydrous magnesium sulfate, and then concentrated. The residue was subjected to silica gel column chromatography to give 0.3 g of 4-(2-pentynyloxy)-6-(1,2-dimethyl-2-propenyloxy)pyrimidine.

4-(2-Pentynyloxy)-6-(1,2-dimethyl-2-propenyloxy)pyrimidine

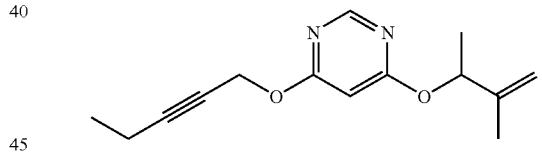

¹H-NMR: 1.15 (t, 3H), 1.43 (d, 3H), 1.78 (s, 3H), 2.24 (qt, 2H), 4.87 (s, 1H), 4.97 (t, 2H), 5.00 (s, 1H), 5.54 (q, 1H), 6.13 (s, 1H), 8.42 (s, 1H).

The following will describe some formulation examples wherein parts represent parts by weight. The present compounds are designated by their compound numbers shown in Tables 1 and 2.

Formulation Example 1

Emulsifiable Concentrate

Nine parts of each of the present compounds (1) to (40) is dissolved in 37.5 parts of xylene and 37.5 parts of dimethylformamide, and 10 parts of polyoxyethylene styryl phenyl ether and 6 parts of calcium dodecylbenzenesulfonate are added thereto, followed by well stirring and mixing, to give an emulsifiable concentrate for each compound.

Formulation Example 2

Wettable Powder

Nine parts of each of the present compounds (1) to (40) is added to a mixture containing 4 parts of sodium laurylsulfate, 2 parts of calcium lignin sulfonate, 20 parts of synthetic hydrated silicone oxide fine powder, and 65 parts of diatomaceous earth, followed by well stirring and mixing, to give a wettable powder for each compound.

Formulation Example 3

Granule

To 3 parts of each of the present compounds (1) to (40) are added 5 parts of synthetic hydrated silicon oxide fine powder, 5 parts of sodium dodecylbenzenesulfonate, 30 parts of bentonite, and 57 parts of clay, followed by well stirring and mixing, and an appropriate amount of water is added to this mixture, followed by further stirring, granulation with a granulator, and air drying, to give a granule for each compound.

Formulation Example 4

Dust

First, 4.5 parts of each of the present compounds (1) to (40), 1 part of synthetic hydrated silicon oxide fine powder, 1 part of Doriresu B (Sankyo Co., Ltd.) as a flocculant, and 7 parts of clay are well mixed with a mortar, followed by stirring and mixing with a mixer. To the resulting mixture is added 86.5 parts of cut clay, followed by well stirring and mixing, to give a dust for each compound.

Formulation Example 5

Ten parts of each of the present compounds (1) to (40), 35 parts of white carbon containing 50 parts of polyoxyethylene alkyl ether sulfate ammonium salt, and 55 parts of water are mixed and pulverized by the wet grinding method to give a formulation for each compound.

The following test example will demonstrate that the present compounds have excellent pesticidal activity.

Test Example 1

Ten parts of each of the present compounds (1) to (6), (8) to (23), (30), (31), and (34) to (40); white carbon containing 50 parts of polyoxyethylene alkyl ether sulfate ammonium salt; and 55 parts of water were mixed and pulverized by the wet grinding method to give a formulation for each compound. The formulation of each present compound was diluted with water so that the active ingredient concentration came to 500 ppm to prepare a spray solution.

A polyethylene cup was seeded with cucumber and a plant was grown until the first true leaf was developed, on which about twenty *Aphis gossypii* (cotton aphid) are allowed to be parasitic. On the next day, the above spray solution was applied at a ratio of 20 ml/cup to the cucumber plant. On the sixth day after the application, the number of *Aphis gossypii* was examined and the preventive value was determined by the following equation:

$$\text{Preventive value (\%)} = \{1 - (Cb \times Tai)/(Cai \times Tb)\} \times 100$$

where the variables in the equation have the following meanings:

Cb: the number of pests before treatment in an untreated area

Cai: the number of pests when observed in the untreated area

Tb: the number of pests before treatment in a treated area

Tai: the number of pests when observed in the treated area.

As a result, all the present compounds (1) to (6), (8) to (23), (30), (31), and (34) to (40) exhibited the preventive value of 90% or higher.

Test Example 2

Ten parts of each of the present compounds (2), (4), (6), (7), (8), (11), (12), (14), (16), (17), (19) to (24), (26), (28), (29), (34), (36) to (38), and (40); white carbon containing 50 parts of polyoxyethylene alkyl ether sulfate ammonium salt; and 55 parts of water were mixed and pulverized by the wet grinding method to give a formulation for each compound. The formulation of each present compound was diluted with water so that the active ingredient concentration came to 500 ppm to prepare a spray solution.

A polyethylene cup was seeded with cucumber and a plant was grown until the first true leaf was developed, to which the above spray solution was applied at a ratio of 20 ml/cup. After the chemical solution sprayed to the cucumber were dried, the first true leaf was cut off and placed on a filter paper (70 mm in diameter) impregnated with water in a polyethylene cup (110 mm in diameter). Thirty larvae of *Frankliniella occidentalis* (Western flower thrips) were set free on the first true leaf, which was covered with a polyethylene cup. After seven days, the number of surviving pests was examined.

As a result, the number of surviving pests was 0 on the leaves treated with each of the present compounds (2), (4), (6), (7), (8), (11), (12), (14), (16), (17), (19) to (24), (26), (28), (29), (34), (36) to (38), and (40).

Test Example 3

Ten parts of each of the present compounds (2) to (8), (10) to (32) and (34) to (40); white carbon containing 50 parts of polyoxyethylene alkyl ether sulfate ammonium salt; and 55 parts of water were mixed and pulverized by the wet grinding method to give a formulation for each compound formulation of each present compound was diluted with water so that the active ingredient concentration came to 500 ppm to prepare a spray solution.

A polyethylene cup was seeded with cabbage and a plant was grown until the first true leaf was developed. The first true leaf was left, while the other leaves were cut off. Adults of *Bemisia argentifolii* (silverleaf whitefly) were set free on the first true leaf and allowed to lay eggs for about 24 hours. The cabbage leaf with about 80 to 100 eggs thus laid thereon was kept in a greenhouse. On eighth day after, when greater part of the larvae were hatching from the laid eggs, the above spray solution was applied at a ratio of 20 ml/cup to the cabbage plant. On the seventh day after the application, the number of surviving larvae was counted.

As a result, the number of surviving larvae was not greater than 10 on the cabbage leaves treated with each of the present compounds (2) to (8), (10) to (32) and (34) to (40).

Test Example 4

Ten parts of each of the present compounds (1) to (23) and (25) to (40); white carbon containing 50 parts of polyoxyethylene alkyl ether sulfate ammonium salt; and 55 parts of water were mixed and pulverized by the wet grinding method to give a formulation for each compound. The formulation of each present compound obtained according to Formulation Example 5 was diluted so that the active ingredient concentration came to 500 ppm to prepare a spray solution.

Fifty grams of molding Bonsoru 2 (available from Sumitomo Chemical Co., Ltd.) was put into a polyethylene cup, and 10 to 15 seeds of rice were planted in the polyethylene cup. Then rice plants were grown until the second foliage leaves developed and then cut into the same height of 5 cm. The above spray solution was applied at the rate of 20 ml/cup to these rice plants. After the chemical solution sprayed onto the rice plants were dried, thirty first-instar larvae of *Nilaparvata lugens* (brown planthopper) were set free on the rice plants, which was then left in a greenhouse at 25° C. On the sixth day after the release of larvae of *Nilaparvata lugens*, the number of parasitic *Nilaparvata lugens* on the rice plants was examined.

As a result, in the treatment with each of the present compounds (1) to (23) and (25) to (40), the number of parasitic *Nilaparvata lugens* on the sixth day after the treatment was not greater than 3.

INDUSTRIAL APPLICABILITY

The present compounds have excellent pesticidal activity, and therefore, they are useful as the active ingredients of pesticidal compositions.

The invention claimed is:

1. A pyrimidine compound of formula (1):

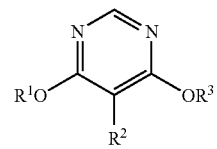

wherein $R^1$ is $C_3$–$C_7$ alkynyl; $R^2$ is hydrogen, halogen, or $C_1$–$C_3$ alkyl; and $R^3$ is $C_1$–$C_8$ alkyl that may be substituted with halogen or $C_1$–$C_3$ alkoxy, or $C_3$–$C_6$ cycloalkyl—(that may be substituted with halogen or $C_1$–$C_3$ alkyl) $C_1$–$C_3$ alkyl.

2. The pyrimidine compound according to claim 1, wherein $R^1$ is $C_3$–$C_7$ alkynyl in which the bond between the carbon atoms at positions 2 and 3 is a triple bond.

3. The pyrimidine compound according to claim 1, wherein $R^1$ is 2-butynyl, 2-pentynyl, 1-methyl-2-butynyl or 1-methyl-2-pentynyl.

4. The pyrimidine compound according to any one of claims 1 to 3, wherein $R^2$ is hydrogen.

5. A pesticidal composition comprising a pyrimidine compound according to claim 1 as an active ingredient.

6. A method for controlling pests comprising applying a pyrimidine compound according to claim 1 to pests or habitats of pests.

\* \* \* \* \*